US010736788B2

(12) United States Patent
Locke et al.

(10) Patent No.: US 10,736,788 B2
(45) Date of Patent: *Aug. 11, 2020

(54) DRESSING WITH CONTRACTING LAYER FOR LINEAR TISSUE SITES

(71) Applicant: KCI Licensing, Inc., San Antonio, TX (US)

(72) Inventors: Christopher Brian Locke, Bournemouth (GB); Timothy Mark Robinson, Shillingstone (GB); Robert Tuck, Hampshire (GB); Gareth Stephenson, Southampton (GB)

(73) Assignee: KCI Licensing, Inc., San Antonio, TX (US)

( * ) Notice: Subject to any disclaimer, the term of this patent is extended or adjusted under 35 U.S.C. 154(b) by 154 days.

This patent is subject to a terminal disclaimer.

(21) Appl. No.: 15/958,773

(22) Filed: Apr. 20, 2018

(65) Prior Publication Data

US 2018/0235815 A1     Aug. 23, 2018

Related U.S. Application Data

(63) Continuation of application No. 14/708,061, filed on May 8, 2015, now Pat. No. 9,974,694.

(Continued)

(51) Int. Cl.
    *A61F 13/00*     (2006.01)
    *A61M 1/00*      (2006.01)

(52) U.S. Cl.
    CPC .. *A61F 13/00068* (2013.01); *A61F 13/00017* (2013.01); *A61F 13/00042* (2013.01); *A61M 1/0088* (2013.01)

(58) Field of Classification Search
    CPC ........... A61F 13/00042; A61F 13/0216; A61F 2013/00255; A61F 13/00068;

(Continued)

(56) References Cited

U.S. PATENT DOCUMENTS 1,355,846 A    10/1920   Rannells
2,547,758 A     4/1951   Keeling
(Continued)

FOREIGN PATENT DOCUMENTS

AU         550575 B2      3/1986
AU         745271 B2      3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Katrina M Stransky

(57) ABSTRACT

Systems, apparatuses, and methods for closing an opening through a surface of a tissue site are described. The system includes a sealing member adapted to cover the opening to form a sealed space and a negative-pressure source adapted to be fluidly coupled to the sealed space to provide negative pressure to the sealed space. The system also includes a contracting layer adapted to be positioned adjacent the opening and formed from a material having a firmness factor and a plurality of holes extending through the contracting layer to form a void space. The holes have a perforation shape factor and a strut angle causing the plurality of holes to collapse in a direction substantially perpendicular to the opening. The contracting layer generates a closing force substantially parallel to the surface of the tissue site to close the opening in response to application of the negative pressure.

21 Claims, 14 Drawing Sheets

Related U.S. Application Data

(60) Provisional application No. 61/991,174, filed on May 9, 2014.

(58) Field of Classification Search
CPC ........ A61F 13/00029; A61F 13/00017; A61M 1/0088; A61M 1/009
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Canon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,974,694 B2 * | 5/2018 | Locke ................ A61M 1/0088 |
| 2001/0037118 A1 | 11/2001 | Shadduck |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0177253 A1 | 7/2008 | Boehringer et al. |
| 2008/0275409 A1 | 11/2008 | Kane et al. |
| 2009/0093779 A1 | 4/2009 | Riesinger |
| 2010/0063484 A1 | 3/2010 | Heagle |
| 2010/0160871 A1 | 6/2010 | Seegert et al. |
| 2010/0160874 A1 | 6/2010 | Robinson et al. |
| 2010/0185163 A1 | 7/2010 | Heagle |
| 2011/0178451 A1 | 7/2011 | Robinson et al. |
| 2011/0213319 A1 | 9/2011 | Blott et al. |
| 2011/0230809 A1 | 9/2011 | Manwaring et al. |
| 2012/0143113 A1 | 6/2012 | Robinson et al. |
| 2012/0143114 A1 | 6/2012 | Locke et al. |
| 2013/0274717 A1 | 10/2013 | Dunn |
| 2014/0066868 A1 | 3/2014 | Freedman et al. |
| 2014/0163491 A1 | 6/2014 | Schuessler et al. |
| 2015/0080788 A1 | 3/2015 | Blott et al. |

(56) References Cited

U.S. PATENT DOCUMENTS

| | | | |
|---|---|---|---|
| 2015/0201954 A1 | 7/2015 | Pratt et al. | |
| 2017/0189237 A1 | 7/2017 | Locke et al. | |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| DE | 102006017194 A1 | 10/2007 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 2098257 A1 | 9/2009 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2365350 A | 2/2002 | |
| GB | 2377939 A | 1/2003 | |
| JP | S57-013040 A | 1/1982 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2008005532 A2 | 1/2008 | |
| WO | 2008136998 A1 | 11/2008 | |
| WO | 2009021523 A1 | 2/2009 | |
| WO | 2010051073 A1 | 5/2010 | |
| WO | 2010/075178 A2 | 7/2010 | |
| WO | 2013066426 A2 | 5/2013 | |
| WO | 2013071243 A2 | 5/2013 | |
| WO | 2013116552 A1 | 8/2013 | |
| WO | 2013129343 A1 | 9/2013 | |
| WO | 2014014871 A1 | 1/2014 | |
| WO | WO 2014/014922 A1 * | 1/2014 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for PCT/US2015/030027 dated Jul. 15, 2015.
Partial International Search Report from PCT/US2015/030030 dated Jul. 22, 2015.
International Search Report and Written Opinion for PCT/US2015/030023 dated Aug. 24, 2015.
Extended European Search Report for corresponding Application No. 171862527, dated Nov. 14, 2017.
"Introduction to Polyurethanes: Thermoplastic Polyurethane", American Chemistry Council, https://polyurethane.americanchemistry.com/polyurethanes/Introduction-to-Polyurethanes/Applications/Thermoplastic-Polyurethane/.
International Search Report and Written Opinion for corresponding Application No. PCT/US2019/027463, dated Jul. 4, 2019.
Japanese Notice of Rejection for corresponding Application No. 2016-566815, dated Feb. 5, 2019.
Extended European Search Report for corresponding Application No. 18162504.7, dated May 24, 2018.
Japanese Notice of Rejection for corresponding Application No. 2016-566785, dated Jun. 25, 2019.
Japanese Notice of Rejection for corresponding Application No. 2016-566785, dated Jan. 29, 2019.

\* cited by examiner

---

DRESSING WITH CONTRACTING LAYER FOR LINEAR TISSUE SITES

This application is a continuation of U.S. patent application Ser. No. 14/708,061, filed May 8, 2015, which claims the benefit, under 35 USC § 119(e), of the filing of U.S. Provisional Patent Application Ser. No. 61/991,174, entitled "Dressing with Contracting Layer for Linear Tissue Sites," by Locke et al., filed May 9, 2014, which is incorporated herein by reference for all purposes.

TECHNICAL FIELD

The invention set forth in the appended claims relates generally to tissue treatment systems and more particularly, but without limitation, to a dressing having a contracting layer for assisting in closure of linear tissue sites.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for closing an opening through a surface of a tissue site are set forth in the appended claims. Illustrative embodiments are also provided to enable a person skilled in the art to make and use the claimed subject matter. For example, a system for closing an opening through a surface of a tissue site is described. The system may include a sealing member adapted to cover the opening to form a sealed space and a negative-pressure source adapted to be fluidly coupled to the sealed space to provide negative pressure to the sealed space. The system can include a protective layer adapted to be positioned adjacent to the opening. The system may also include a contracting layer adapted to be positioned adjacent to the protective layer and formed from a material having a firmness factor and a plurality of holes extending through the contracting layer to form a void space. The holes may have a perforation shape factor and a strut angle causing the plurality of holes to collapse in a direction substantially perpendicular to the opening. The contracting layer may generate a closing force substantially parallel to the surface of the tissue site to close the opening in response to application of the negative pressure.

Alternatively, other example embodiments may include an apparatus for closing an opening through a surface of a tissue site. The apparatus may include a contracting layer adapted to be positioned adjacent the opening and formed from a material having a firmness factor and a plurality of holes extending through the contracting layer to form a void space. The holes may have a perforation shape factor and a strut angle causing the plurality of holes to collapse in a direction substantially perpendicular to the opening. The contracting layer may generate a closing force substantially parallel to the surface of the tissue site to close the opening in response to application of a negative pressure.

A method for closing an opening through a surface of a tissue site is also described. The method may include positioning a contracting layer adjacent to and covering the tissue site. The contracting layer may be adapted to be positioned adjacent the opening and formed from a material having a firmness factor and a plurality of holes extending through the contracting layer to form a void space. The holes may have a perforation shape factor and a strut angle causing the plurality of holes to collapse in a direction substantially perpendicular to the opening. The contracting layer may be collapsed parallel to the surface of the tissue site to generate a closing force.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
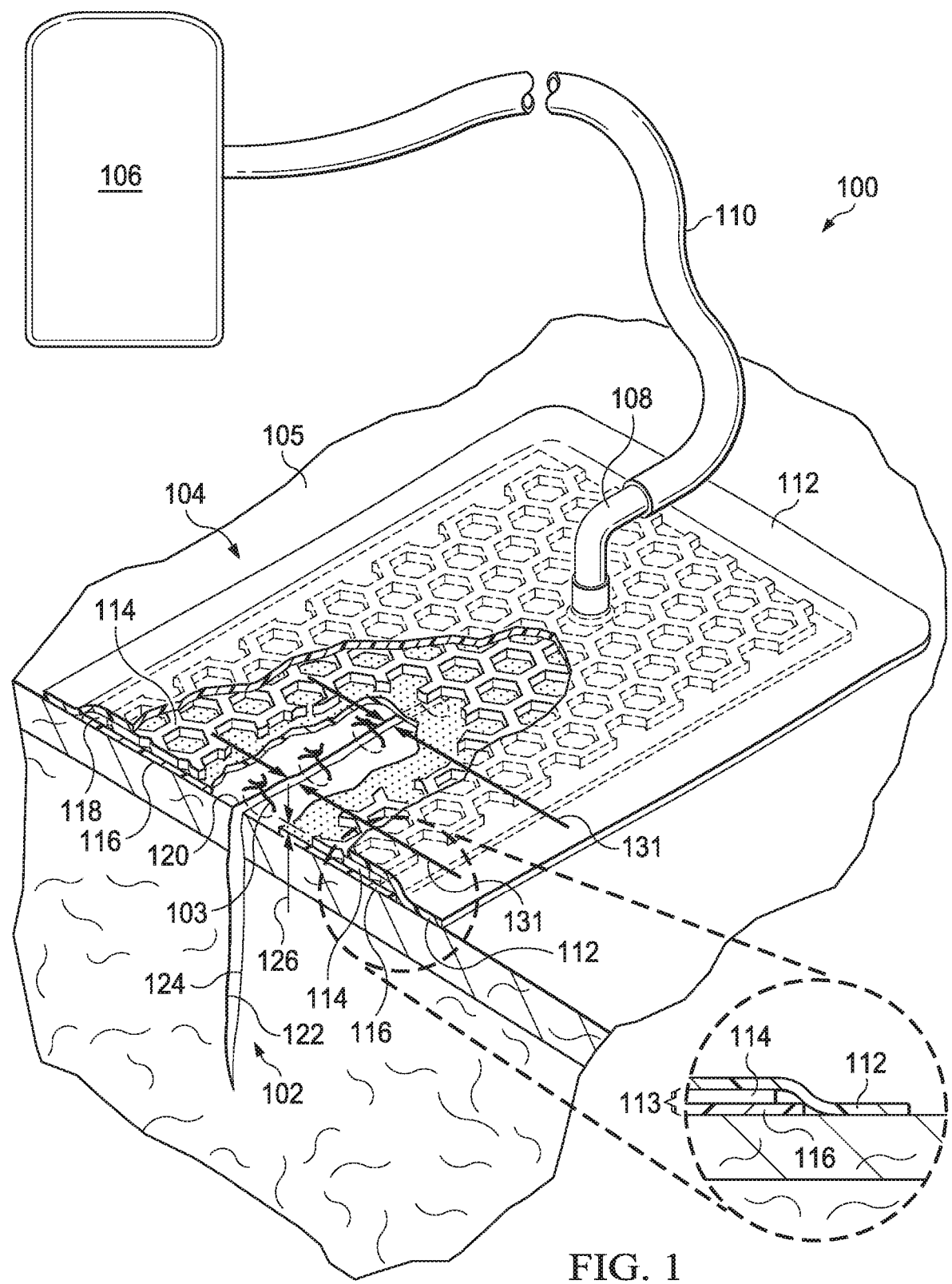
FIG. 1 is a perspective section view with a portion show in elevation, illustrating details that may be associated with some embodiments of a negative-pressure therapy system.

FIG. 1 illustrates details that may be associated with some embodiments of a negative-pressure therapy system 100 that can be applied to a tissue site 102. In some embodiments, the tissue site 102 may be closed by one or more stitches 103. The negative-pressure therapy system 100 may include a dressing and a negative-pressure source. For example, a dressing 104 may be fluidly coupled to a negative-pressure source 106, as illustrated in FIG. 1. A dressing may be fluidly coupled to a negative-pressure source by a connector and a tube. The dressing 104, for example, may be fluidly coupled to the negative-pressure source 106 by a connector 108 and a tube 110. A dressing may generally include a cover and a tissue interface. The dressing 104, for example, may include a cover 112 and a tissue interface 113. In some embodiments, the tissue interface 113 may include a contracting layer, such as a contracting layer 114, and a protective layer, such as a protective layer 116.

In general, components of the negative-pressure therapy system 100 may be coupled directly or indirectly. For example, the negative-pressure source 106 may be directly coupled to the dressing 104 and indirectly coupled to the tissue site 102 through the dressing 104. Components may be fluidly coupled to each other to provide a path for transferring fluids (i.e., liquid and/or gas) between the components.

In some embodiments, components may be fluidly coupled through a tube, such as the tube 110. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, a tissue interface, such as the tissue interface 113, may be placed within, over, on, or otherwise proximate to a tissue site. A cover may be placed over a tissue interface and sealed to tissue near a tissue site. For example, the tissue interface 113 may be placed over the tissue site 102, and the cover 112 may be sealed to undamaged epidermis peripheral to the tissue site 102. Thus, the cover 112 can provide a sealed therapeutic environment 118 proximate to the tissue site 102 that is substantially isolated from the external environment, and the negative-pressure source 106 can reduce the pressure in the sealed therapeutic environment 118.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically refers to a position in a fluid path relatively closer to a negative-pressure source. Conversely, the term "upstream" refers to a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or a defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used at a tissue site to grow additional tissue that may be harvested and transplanted to a tissue site at another location.

A tissue site may also be characterized by shape. For example, some tissue sites may be referred to as a linear tissue site. A linear tissue site may generally refer to a tissue site having an elongated shape, such as an incision having a length substantially greater than its width. An incision may have edges that may be substantially parallel, particularly if the incision is caused by a scalpel, knife, razor, or other sharp blade. Other examples of a linear tissue site may include a laceration, a puncture, or other separation of tissue, which may have been caused by trauma, surgery, or degeneration. In some embodiments, a linear tissue site may also be an incision in an organ adjacent a fistula. In some embodiments, a linear tissue site may be an incision or puncture in otherwise healthy tissue that extends up to 40 cm or more in length. In some embodiments, a linear tissue site may also vary in depth. For example, an incision may have a depth that extends up to 15 cm or more or may be subcutaneous depending on the type of tissue and the cause of the incision.

The tissue site 102, for example, may illustrate a linear tissue site having a tissue surface 105 and an opening 120 through the tissue surface 105 along a length of the tissue site 102. The tissue site 102 may also have a first wall 122 and a second wall 124 extending from the opening 120 in the tissue surface 105 generally parallel to each other along the length and depth of the tissue site 102.

In some embodiments, one or more stitches 103 may be used to close the opening 120. The stitches 103 may be surgical sutures, for example, which may be used to hold tissue together following an injury or a surgical procedure. Generally, stitches may be thread formed from absorbable material such as polyglycolic acid, polylactic acid, monocryls, and polydioxanone, or non-absorbable materials such as nylon, polyester, polyvinylidene fluoride, and polypropylene. The stitches 103 may apply a closing force to the opening 120 by being placed under tension to draw the first wall 122 and the second wall 124 toward each other.

"Negative pressure" generally refers to a pressure less than a local ambient pressure. A local ambient pressure may be a pressure in a local environment external to the sealed therapeutic environment 118 provided by the dressing 104. In many cases, a local ambient pressure may also be the atmospheric pressure at which a tissue site is located. Alternatively, negative pressure may be a pressure that is less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 106, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A tissue interface, such as the contracting layer 114 or the protective layer 116, can generally be adapted to contact a tissue site. A tissue interface may be partially or fully in contact with a tissue site. If a tissue site is a wound, for example, a tissue interface may partially or completely fill the wound, or may be placed over the wound. A tissue interface may take many forms, and may have many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

In some embodiments, a tissue interface may be a manifold or may include a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which a tissue interface may be made from a hydrophilic material, the tissue interface may also wick fluid away from a tissue site, while continuing to distribute negative pressure to the tissue site. The wicking properties of a tissue interface may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site when pressure within the sealed therapeutic environment is reduced. For example, any or all of the surfaces of a tissue interface may have an uneven, coarse, or jagged profile that can induce microstrains and stresses at a tissue site if negative pressure is applied through a tissue interface. In some embodiments, a tissue interface may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. A tissue interface may further serve as a scaffold for new cell-growth, or a scaffold material may be used in conjunction with the tissue interface to promote cell-growth.

A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 112 may provide a bacterial barrier and protection from physical trauma. The cover 112 may also be constructed from a material that can reduce evaporative losses and provide a fluid seal between two components or two environments, such as between a therapeutic environment and a local external environment. The cover 112 may be, for example, an elastomeric film or membrane that can provide a seal adequate to maintain a negative pressure at a tissue site for a given negative-pressure source. In some example embodiments, the cover 112 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

An attachment device may be used to attach the cover 112 to an attachment surface, such as undamaged epidermis, a gasket, or another cover. In some embodiments, an attachment surface may be tissue surrounding a tissue site, such as the tissue surface 105 surrounding the opening 120. An attachment device may take many forms. For example, an attachment device may be a medically-acceptable, pressure-sensitive adhesive that extends about a periphery, a portion, or an entire sealing member. In some embodiments, for example, some or all of the cover 112 may be coated with an acrylic adhesive having a coating weight between about 25 grams per square meter (gsm) and about 65 gsm. Thicker adhesives or combinations of adhesives may be applied in some embodiments to improve the seal and reduce leaks. Other example embodiments of an attachment device may include a double-sided tape, paste, hydrocolloid, hydrogel, silicone gel, or organogel.

A linear tissue site, such as an incision, may often be created during a surgical procedure if a surgeon or other clinician uses a cutting instrument, such as a scalpel, to pierce and cut through at least a portion of a tissue site. Following a surgical procedure, a closing force may be applied to an opening of an incision to facilitate healing. A closing force may be a force that is substantially parallel to the tissue surface 105 and urges the first wall 122 and the second wall 124 toward each other to close the opening 120. Closure of an opening may help maintain a healing environment for internal structures of a tissue site, as well as inhibit entry of bacteria or other harmful substances into the tissue site.

Often, a mechanical means may be used to apply a closing force to a tissue site. A mechanical means of closing a tissue site may include sutures, staples, hooks, and other devices configured to apply a closing force. Generally, sutures, staples, and other devices may be configured to apply a closing force to a surface of a tissue site or to other tissue peripheral to the tissue site. For example, a thread may be inserted into punctures and drawn across an opening of an incision. The thread may be held under tension with a knot or other securing mechanism to draw opposing sides of an opening together. Sutures and staples may apply a localized stress to tissue near the punctures where the sutures penetrate tissue. Localized stress associated with punctures can lead to patient discomfort, pain, or additional bleeding. In some extreme cases, such mechanical means may cause additional injury, which may result in dehiscence. Weak or delicate skin may be particularity prone to negative effects associated with mechanical means of closure.

These limitations and others may be addressed by negative-pressure therapy system 100, which can provide a closing force 131 to facilitate closure of a tissue site. In some embodiments, the negative-pressure therapy system 100 may include a dressing that can be placed over other mechanical closure devices, such as stitches, to provide and distribute a closing force generally perpendicular to a linear tissue site, such as an incision. In some embodiments, the negative-pressure therapy system 100 may apply a closing force that urges opposing sides of an opening in a linear tissue site toward each other, thereby at least partially relieving localized stresses that may be caused by punctures and stitches.

The negative-pressure therapy system 100 may be used on the tissue site 102. In some embodiments, the contracting layer 114 may be positioned adjacent to the tissue site 102 so that the contracting layer 114 is in contact with the tissue surface 105 surrounding the opening 120. In some embodiments, the protective layer 116 may be positioned between the contracting layer 114 and the tissue surface 105 surrounding the opening 120.

In some embodiments, the contracting layer 114 may be a substantially flat or substantially planar body. The contracting layer 114 may have a thickness 126. In some embodiments, the thickness 126 may be about 15 mm. In other embodiments, the thickness 126 may be thinner or thicker than about 15 mm as needed for the tissue site 102. In some embodiments, individual portions of the contracting layer 114 may have a minimal tolerance from the thickness 126. In some embodiments, the thickness 126 may have a tolerance of about 2 mm. The contracting layer 114 may be flexible so that the contracting layer 114 may be contoured to a surface of the tissue site 102.

In some embodiments, the contracting layer 114 may be formed from thermoplastic elastomers (TPE), such as styrene ethylene butylene styrene (SEBS) copolymers, or thermoplastic polyurethane (TPU). The contracting layer 114 may be formed by combining sheets of TPE or TPU having a thickness between about 0.2 mm and about 2.0 mm to form a structure having the thickness 126. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the contracting layer 114. In some embodiments, the contracting layer 114 may be formed from a 3D textile, also referred to as a spacer fabric. Suitable 3D textiles may be produced by Heathcoat Fabrics, Ltd., Baltex, and Mueller Textil Group.

In some embodiments, the contracting layer 114 may be formed from a foam. For example, cellular foam, open-cell foam, reticulated foam, or porous tissue collections, may be used to form the contracting layer 114. In some embodiments, the contracting layer 114 may be formed of GranuFoam®, grey foam, or Zotefoam. Grey foam may be a polyester polyurethane foam having about 60 pores per inch (ppi). Zotefoam may be a closed-cell crosslinked polyolefin foam. In one non-limiting example, the contracting layer 114 may be an open-cell, reticulated polyurethane foam such as GranuFoam® dressing available from Kinetic Concepts, Inc. of San Antonio, Tex.; in other embodiments, the contracting layer 114 may be an open-cell, reticulated polyurethane foam such as a VeraFlo® foam, also available from Kinetic Concepts, Inc., of San Antonio, Tex.

In some embodiments, the contracting layer 114 may be formed from a foam that is mechanically or chemically compressed to increase the density of the foam at ambient pressure. A foam that is mechanically or chemically compressed may be referred to as a compressed foam. A compressed foam may be characterized by a firmness factor (FF) that may be defined as a ratio of the density of a foam in a compressed state to the density of the same foam in an uncompressed state. For example, a firmness factor (FF) of 5 may refer to a compressed foam having a density that is five times greater than a density of the same foam in an uncompressed state. Mechanically or chemically compressing a foam may reduce a thickness of the foam at ambient pressure when compared to the same foam that has not been compressed. Reducing a thickness of a foam by mechanical or chemical compression may increase a density of the foam, which may increase the firmness factor (FF) of the foam. Increasing the firmness factor (FF) of a foam may increase a stiffness of the foam in a direction that is parallel to a thickness of the foam. For example, increasing a firmness factor (FF) of the contracting layer 114 may increase a stiffness of the contracting layer 114 in a direction that is parallel to the thickness 126 of the contracting layer 114. In some embodiments, a compressed foam may be a compressed GranuFoam®. GranuFoam® may have a density of about 0.03 grams per centimeter$^3$ (g/cm$^3$) in its uncompressed state. If the GranuFoam® is compressed to have a firmness factor (FF) of 5, the GranuFoam® may be compressed until the density of the GranuFoam® is about 0.15 g/cm$^3$. VeraFlo® foam may also be compressed to form a compressed foam having a firmness factor (FF) up to 5.

The firmness factor (FF) may also be used to compare compressed foam materials with non-foam materials. For example, a Supracor® material may have a firmness factor (FF) that allows Supracor® to be compared to compressed foams. In some embodiments, the firmness factor (FF) for a non-foam material may represent that the non-foam material has a stiffness that is equivalent to a stiffness of a compressed foam having the same firmness factor. For example, if a contracting layer is formed from Supracor®, as illustrated in Table 1 below, the contracting layer may have a stiffness that is about the same as the stiffness of a compressed GranuFoam® material having a firmness factor (FF) of 3.

Generally, if a compressed foam is subjected to negative pressure, the compressed foam exhibits less deformation than a similar uncompressed foam. If the contracting layer 114 is formed of a compressed foam, the thickness 126 of the contracting layer 114 may deform less than if the contracting layer 114 is formed of a comparable uncompressed foam. The decrease in deformation may be caused by the increased stiffness as reflected by the firmness factor (FF). If subjected to the stress of negative pressure, the contracting layer 114 formed of compressed foam may flatten less than the contracting layer 114 that is formed from uncompressed foam. Consequently, when negative pressure is applied to the contracting layer 114, the stiffness of the contracting layer 114 in the direction parallel to the thickness 126 of the contracting layer 114 allows the contracting layer 114 to be more compliant or compressible in other directions, e.g., a direction parallel to the tissue surface 105 or in a direction perpendicular to the opening 120 of the tissue site 102. The foam material used to form a compressed foam may be either hydrophobic or hydrophilic. The pore size of a foam material may vary according to needs of the contracting layer 114 and the amount of compression of the foam. For example, in some embodiments, an uncompressed foam may have pore sizes in a range of about 400 microns to about 600 microns. If the same foam is compressed, the pore sizes may be smaller than when the foam is in its uncompressed state.

The protective layer 116 may be a layer of material positioned between the contracting layer 114 and the tissue site 102. In some embodiments, the protective layer 116 may be coextensive with the contracting layer 114. In other embodiments, the protective layer 116 may be larger or smaller than the contracting layer 114. In some embodiments, the protective layer 116 may have a thickness that is less than the thickness 126 of the contracting layer 114. In sonic embodiments, the protective layer 116 may be a protective mesh, a perforated film, a woven material or a non-woven material. In some embodiments, the protective layer 116 may be laminated to the contracting layer 114. In some embodiments, the protective layer 116 may inhibit irritation of the tissue site 102.

Figure 2:
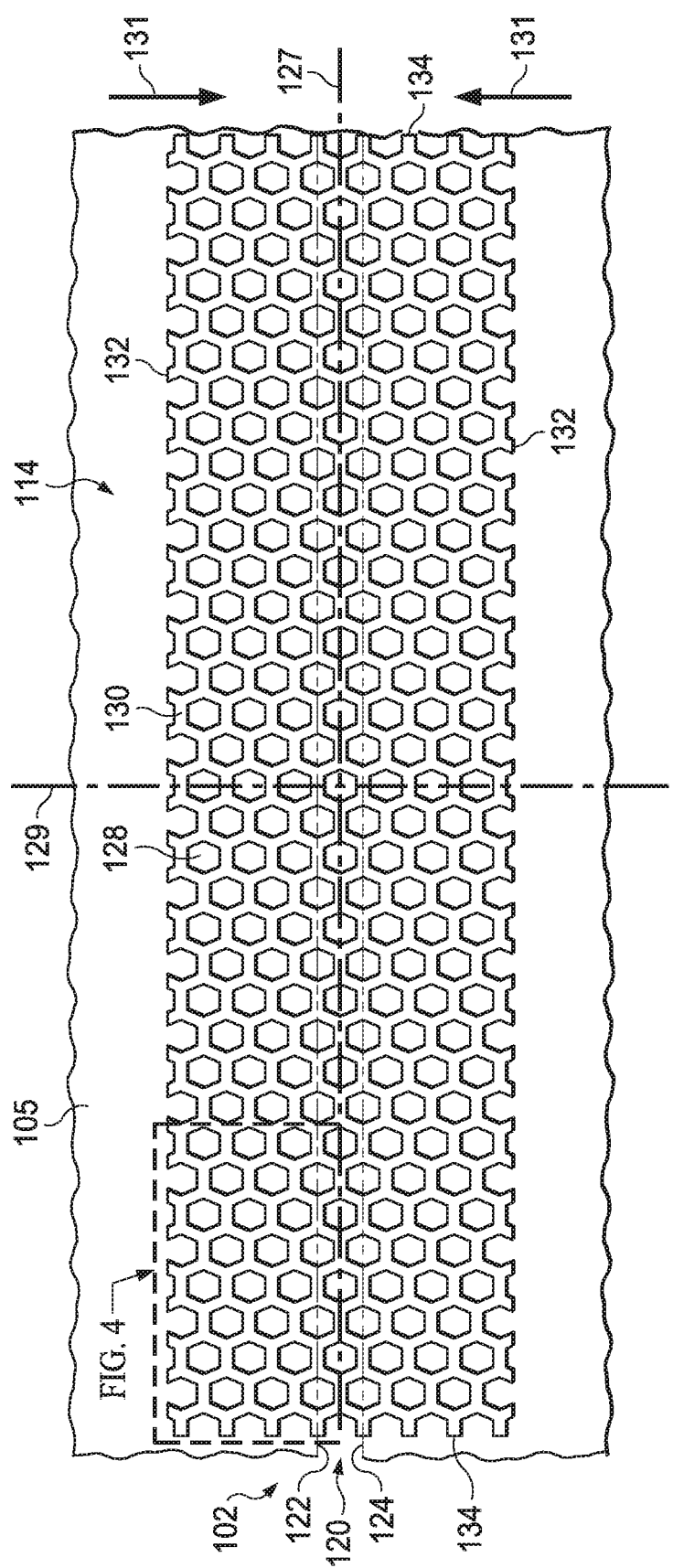
FIG. 2 is a plan view, illustrating details that may be associated with some embodiments of a contracting layer of the negative-pressure therapy system of FIG. 1 in a first position.

FIG. 2 is a plan view, illustrating additional details that may be associated with some embodiments of the contracting layer 114. The contracting layer 114 may include a plurality of holes 128 or perforations extending through the contracting layer 114 to form walls 130 extending through the contracting layer 114. In some embodiments, the walls 130 may be generally parallel to the thickness 126 of the contracting layer 114. In other embodiments, the walls 130 may be generally perpendicular to the surface of the contracting layer 114. In some embodiments, the holes 128 may have a hexagonal shape as shown.

The contracting layer 114 may cover the opening 120 in the tissue surface 105 of the tissue site 102. In some embodiments, the contracting layer 114 may have a first orientation line 127 and a second orientation line 129 that is perpendicular to the first orientation line 127. In some embodiments, an orientation line, such as the first orientation line 127 or the second orientation line 129, may be a line of symmetry of the contracting layer 114. A line of symmetry may be, for example, an imaginary line across a surface of the contracting layer 114 defining a fold line such that if the contracting layer 114 is folded on the line of symmetry, the holes 128 and the walls 130 would be coincidentally aligned. Generally, if the dressing 104 is being used, the first orientation line 127 and the second orientation line 129 may be lines used to orient the contracting layer 114 relative to the tissue site 102. In some embodiments, the first orientation line 127 and the second orientation line 129 may be used to refer to the desired directions of contraction for the contracting layer 114. For example, if the first orientation line 127 is oriented parallel to the opening 120, the desired direction of contraction may be parallel to the second orientation line 129 and perpendicular to the first orientation line 127. Generally, the contracting layer 114 may be placed at the tissue site 102 so that the first orientation line 127 is parallel to the opening 120 and may cover portions of the tissue surface 105 on both sides of the opening 120. In some embodiments, the first orientation line 127 may be coincident with the opening 120.

Although the contracting layer 114 is shown as having a generally rectangular shape including longitudinal edges 132 and latitudinal edges 134, the contracting layer 114 may have other shapes. For example, the contracting layer 114 may have a diamond, square, or circular shape. In some embodiments, the shape of the contracting layer 114 may be selected to accommodate the type of tissue site being treated.

In some embodiments, the first orientation line 127 may be parallel to the longitudinal edges 132.

Figure 3:
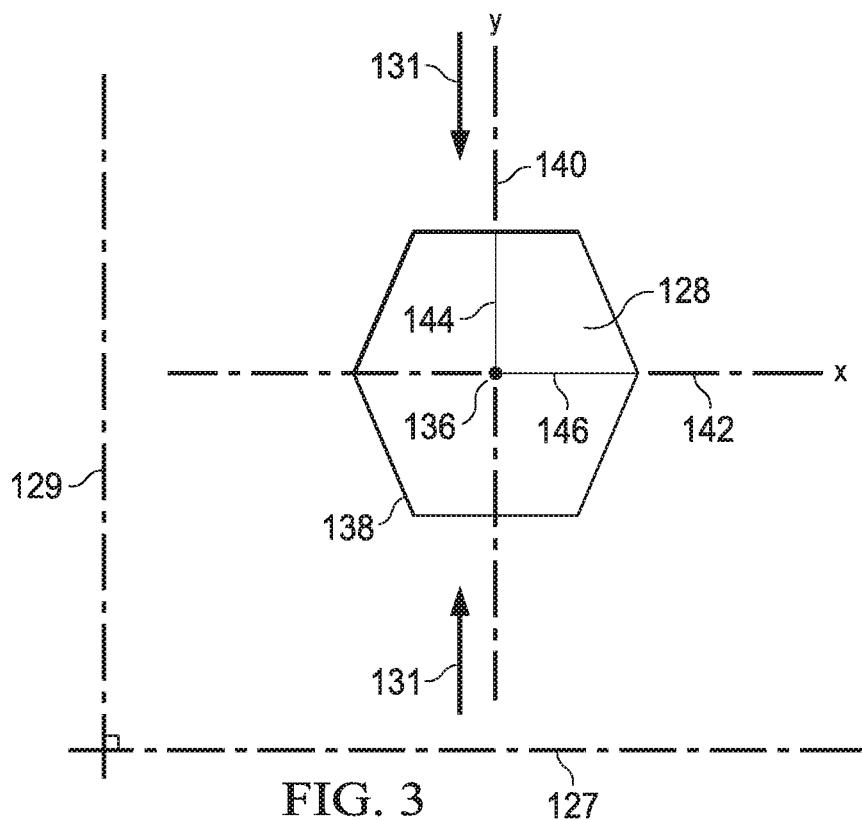
FIG. 3 is a schematic view, illustrating details that may be associated with some embodiments of a hole of the contracting layer of FIG. 2.

Referring more specifically to FIG. 3, a single hole 128 having a hexagonal shape is shown. The hole 128 may include a center 136 and a perimeter 138. The hole 128 may have a perforation shape factor (PSF). The perforation shape factor (PSF) may represent an orientation of the hole 128 relative to the first orientation line 127 and the second orientation line 129. Generally, the perforation shape factor (PSF) is a ratio of ½ a maximum length of the hole 128 that is parallel to the second orientation line 129 to ½ a maximum length of the hole 128 that is parallel to the first orientation line 127. For reference, the hole 128 may have an X-axis 142 extending through the center 136 between opposing vertices of the hexagon and parallel to the first orientation line 127, and a Y-axis 140 extending through the center 136 between opposing sides of the hexagon and parallel to the second orientation line 129. The perforation shape factor (PSF) of the hole 128 may be defined as a ratio of a line segment 144 on the Y-axis 140 extending from the center 136 to the perimeter 138 of the hole 128, to a line segment 146 on the X-axis 142 extending from the center 136 to the perimeter 138 of the hole 128. If a length of the line segment 144 is 2.69 mm and the length of the line segment 146 is 2.5 mm, the perforation shape factor (PSF) would be 2.69/2.5 or about 1.08. In other embodiments, the hole 128 may be oriented relative to the first orientation line 127 and the second orientation line 129 so that the perforation shape factor (PSF) may be about 1.07 or 1.1.

Figure 4:
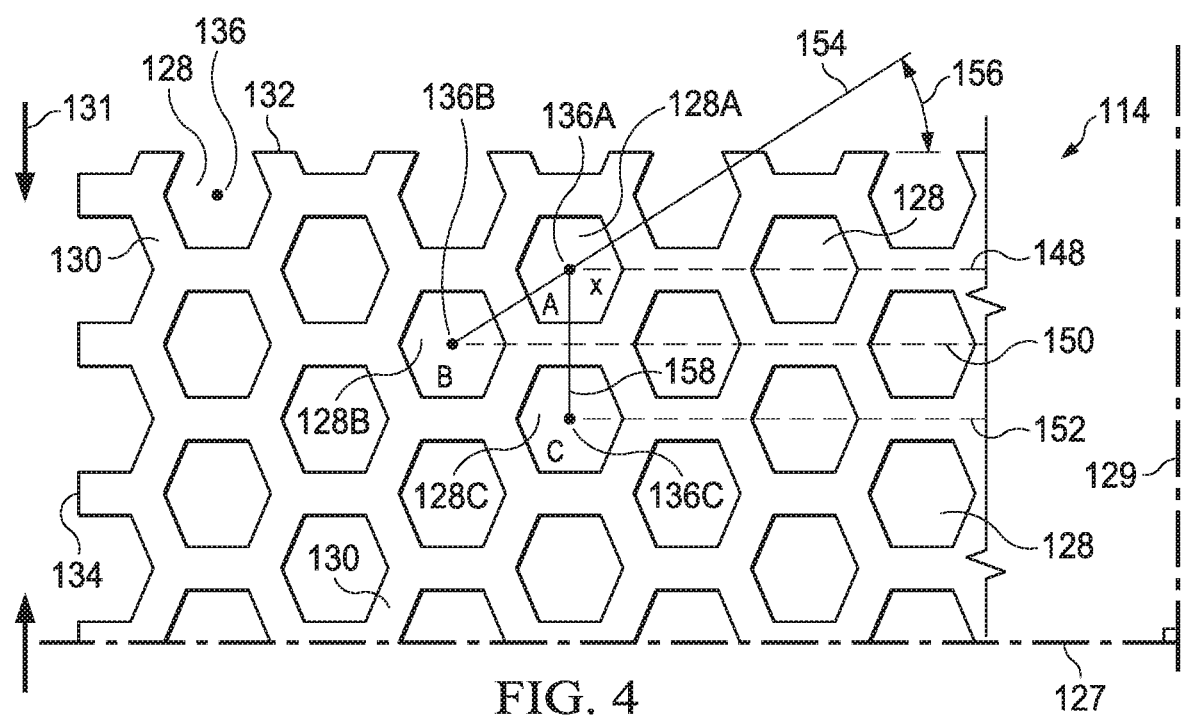
FIG. 4 is a plan view, illustrating details that may be associated with some embodiments of the holes of the contracting layer of FIG. 2.

Referring to FIG. 4, a portion of the contracting layer 114 of FIG. 1 is shown. The contracting layer 114 may include the plurality of holes 128 aligned in a pattern of parallel rows. The pattern of parallel rows may include a first row 148 of the holes 128, a second row 150 of the holes 128, and a third row 152 of the holes 128. The centers 136 of the holes 128 in adjacent rows, for example, the first row 148 and the second row 150, may be characterized by being offset from the second orientation line 129 along the first orientation line 127. In some embodiments, a line connecting the centers of adjacent rows may form a strut angle (SA) with the first orientation line 127. For example, a first hole 128A in the first row 148 may have a center 136A, and a second hole 128B in the second row 150 may have a center 136B. A strut line 154 may connect the center 136A with the center 136B. The strut line 154 may form an angle 156 with the first orientation line 127. The angle 156 may be the strut angle (SA) of the contracting layer 114. In some embodiments, the strut angle (SA) may be less than about 90°. In other embodiments, the strut angle (SA) may be between about 30° and about 70° relative to the first orientation line 127. In other embodiments, the strut angle (SA) may be about 66° from the first orientation line 127. Generally, as the strut angle (SA) decreases, a stiffness of the contracting layer 114 in a direction parallel to the first orientation line 127 may increase. Increasing the stiffness of the contracting layer 114 parallel to the first orientation line 127 may increase the compressibility of the contracting layer 114 perpendicular to the first orientation line 127. Consequently, if negative pressure is applied to the contracting layer 114, the contracting layer 114 may be more compliant or compressible in a direction perpendicular to the first orientation line 127. By increasing the compressibility of the contracting layer 114 in a direction perpendicular to the first orientation line 127, the contracting layer 114 may collapse to apply the closing force 131 to the opening 120 of the tissue site 102, as described in more detail below.

In some embodiments, the centers 136 of the holes 128 in alternating rows, for example, the center 136A of the first hole 128A in the first row 148 and a center 136C of a hole 128C in the third row 152, may be spaced from each other parallel to the second orientation line 129 by a length 158. In some embodiments, the length 158 may be greater than an effective diameter of the hole 128. If the centers 136 of holes 128 in alternating rows are separated by the length 158, the walls 130 parallel to the first orientation line 127 may be considered continuous. Generally, the walls 130 may be continuous if the walls 130 do not have any discontinuities or breaks between holes 128.

Regardless of the shape of the holes 128, the holes 128 in the contracting layer 114 may leave void spaces in the contracting layer 114 and on the surface of the contracting layer 114 so that only the walls 130 of the contracting layer 114 remain with a surface available to contact the tissue surface 105. It may be desirable to minimize the walls 130 so that the holes 128 may collapse, causing the contracting layer 114 to collapse and generate the closing force 131 in a direction perpendicular to the first orientation line 127. However, it may also be desirable not to minimize the walls 130 so much that the contracting layer 114 becomes too fragile for sustaining the application of a negative pressure. The void space percentage (VS) of the holes 128 may be equal to the percentage of the volume or surface area of the void spaces created by the holes 128 to the total volume or surface area of the contracting layer 114. In some embodiments, the void space percentage (VS) may be between about 40% and about 60%. In other embodiments, the void space percentage (VS) may be about 55%.

In some embodiments, the holes 128 may be formed during molding of the contracting layer 114. In other embodiments, the holes 128 may be formed by cutting, melting, or vaporizing the contracting layer 114 after the contracting layer 114 is formed. For example, the holes 128 may be formed in the contracting layer 114 by laser cutting the compressed foam of the contracting layer 114. In some embodiments, an effective diameter of the holes 128 may be selected to permit flow of particulates through the holes 128. An effective diameter of a non-circular area may be defined as a diameter of a circular area having the same surface area as the non-circular area. In some embodiments, each hole 128 may have an effective diameter of about 3.5 mm. In other embodiments, each hole 128 may have an effective diameter between about 5 mm and about 20 mm. The effective diameter of the holes 128 should be distinguished from the porosity of the material forming the walls 130 of the contracting layer 114. Generally, an effective diameter of the holes 128 is an order of magnitude larger than the effective diameter of the pores of a material forming the contracting layer 114. For example, the effective diameter of the holes 128 may be larger than about 1 mm, while the walls 130 may be formed from GranuFoam® material having a pore size less than about 600 microns. In some embodiments, the pores of the walls 130 may not create openings that extend all the way through the material.

Figure 5:
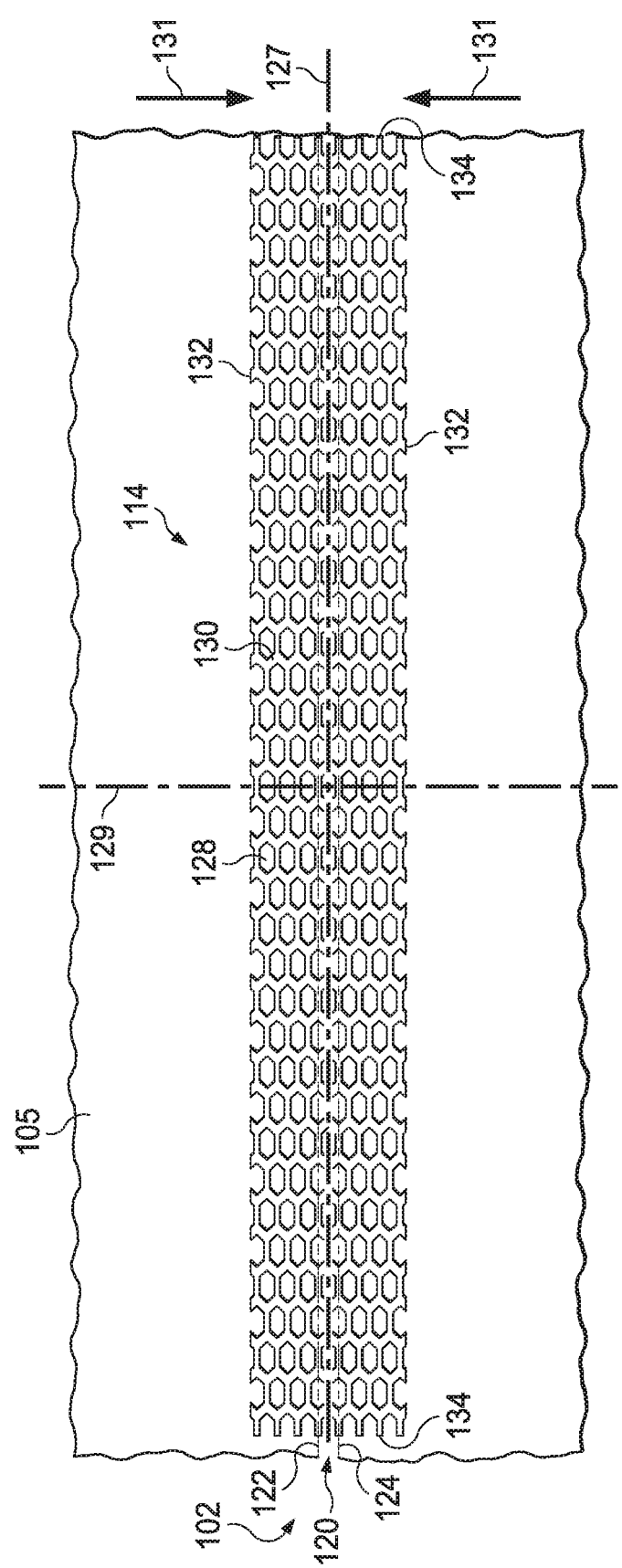
FIG. 5 is a plan view, illustrating details that may be associated with some embodiments of the contracting layer of FIG. 2 in a second position.

Referring now to both FIGS. 2 and 4, the holes 128 may form a pattern depending on the geometry of the holes 128 and the alignment of the holes 128 between adjacent and alternating rows in the contracting layer 114 with respect to the first orientation line 127. If the contracting layer 114 is subjected to negative pressure, the holes 128 of the contracting layer 114 may collapse. In some embodiments void space percentage (VS), the perforation shape factor (PSF), and the strut angle (SA) may cause the contracting layer 114 to collapse along the second orientation line 129 perpendicular to the first orientation line 127 as shown in more detail in FIG. 5. If the contracting layer 114 is positioned on the tissue surface 105 of the tissue site 102 so that the first orientation line 127 coincides with the opening 120, the contracting layer 114 may generate the closing force 131 along the second orientation line 129 such that the tissue surface 105 is contracted in the same direction to facilitate closure of the opening 120 and draw the first wall 122 to the second wall 124 as shown in more detail in FIG. 5. The closing force 131 may be optimized by adjusting the factors described above, as set forth in Table 1 below. In some embodiments, the holes 128 may be hexagonal, have a strut angle (SA) of approximately 66°, a void space percentage (VS) of about 55%, a firmness factor (FF) of 5, a perforation shape factor (PSF) of 1.07, and an effective diameter of about 5 mm. If the contracting layer 114 is subjected to a negative pressure of about −125 mm Hg, the closing force 131 asserted by the contracting layer 114 may be about 13.3 N. If the effective diameter of the holes 128 of the contracting layer 114 is increased to 10 mm, the closing force 131 may be decreased to about 7.5 N.

Figure 6:
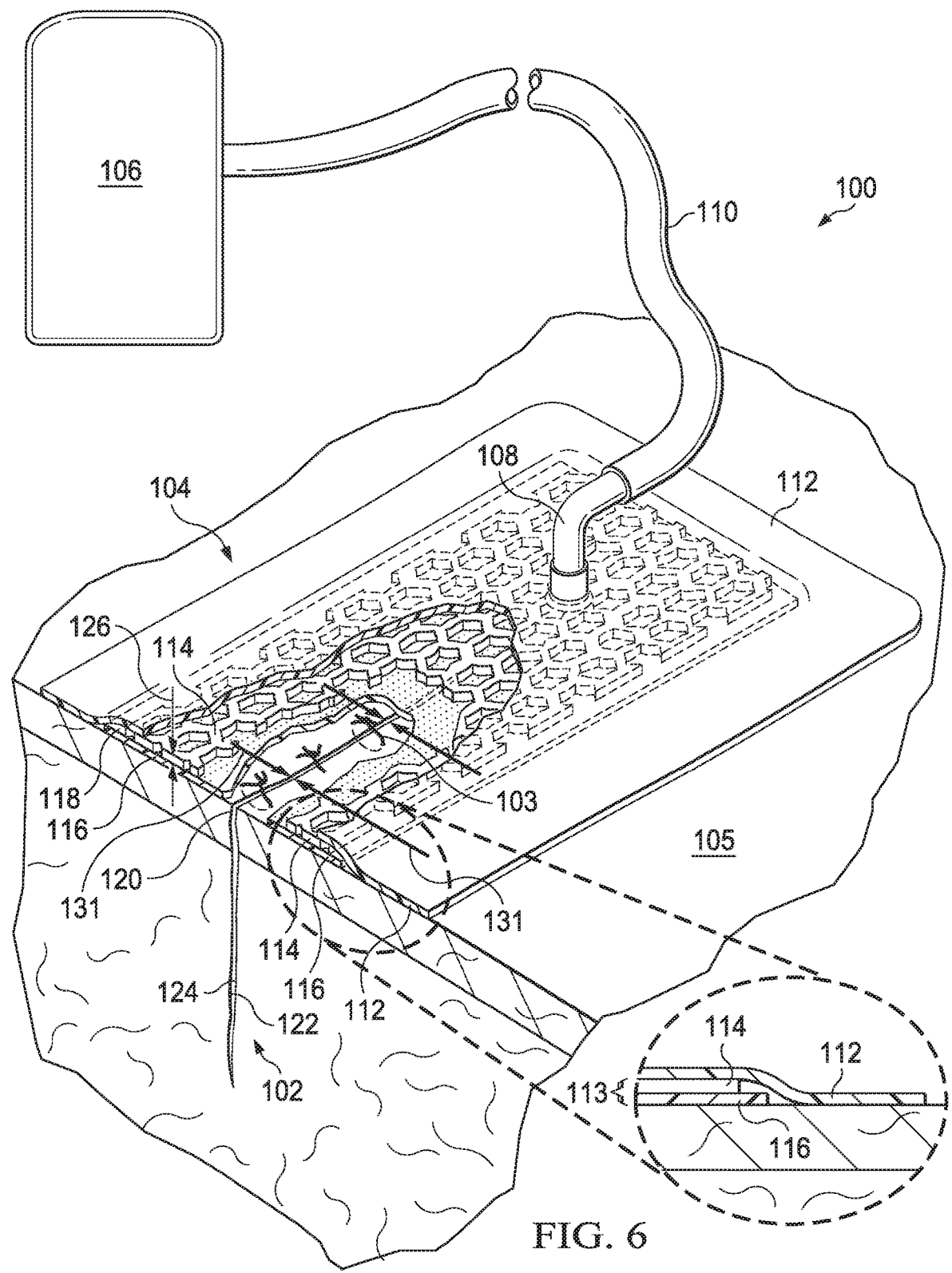
FIG. 6 is a perspective section view with a portion show in elevation, illustrating details that may be associated with some embodiments of the negative-pressure therapy system of FIG. 1.

FIG. 6 is a perspective sectional view with a portion shown in elevation, illustrating additional details that may be associated with some embodiments of the negative-pressure therapy system 100. As shown in FIG. 6, the contracting layer 114 is in the second position, or contracted position, of FIG. 5. In operation, negative pressure may be supplied to the sealed therapeutic environment 118 with the negative-pressure source 106. In response to the supply of negative pressure, the contracting layer 114 may collapse from the position illustrated in FIG. 1 to the position illustrated in FIG. 6. Generally, the thickness 126 of the contracting layer 114 may remain substantially the same. In some embodiments, negative pressure may be supplied to the sealed therapeutic environment 118 until a pressure in the sealed therapeutic environment 118 is about a therapy pressure. In some embodiments, the sealed therapeutic environment 118 may remain at the therapy pressure for a therapy period. In some embodiments, the therapy period may be a time period that allows for opposing sides of the opening 120 to heal. In some embodiments, the therapy period may be cyclic, having a period in which negative pressure may be applied to the tissue site 102 and a period in which negative pressure may be vented from the tissue site 102. In other embodiments, the therapy period may be longer or as shorter as needed to supply appropriate negative-pressure therapy to the tissue site 102.

If the contracting layer 114 is in the second position of FIG. 6, the contracting layer 114 may exert the closing force 131 parallel to the tissue surface 105 of the tissue site 102 toward the opening 120. The closing force 131 may urge the first wall 122 and the second wall 124 toward one another. In some embodiments, the closing force 131 may close the opening 120. The closing force 131 may also relieve localized stresses that may be caused by the stitches 103, reducing the risk of additional trauma to the tissue site 102.

Figure 7:
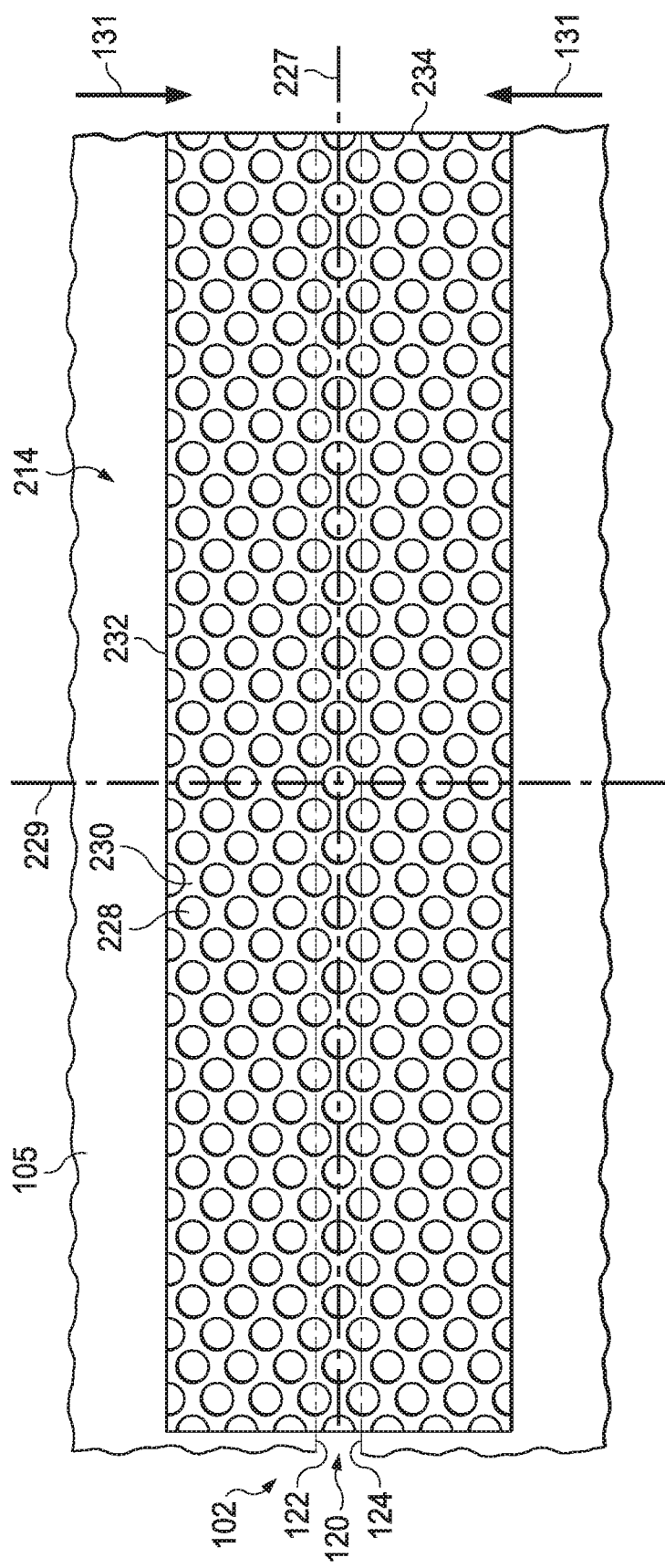
FIG. 7 is a plan view, illustrating details that may be associated with some embodiments of another contracting layer of the negative-pressure therapy system of FIG. 1.

FIG. 7 is a plan view, illustrating additional details that may be associated with some embodiments of a contracting layer 214. The contracting layer 214 may be similar to the contracting layer 114 and operate as described above with respect to FIGS. 1-6. Similar elements may have similar numbers indexed to 200. For example, the contracting layer 214 is shown as having a generally rectangular shape including longitudinal edges 232 and latitudinal edges 234. The contracting layer 214 may have a first orientation line 227 and a second orientation line 229 that is perpendicular to the first orientation line 227. In some embodiments, the first orientation line 227 and the second orientation line 229 may be used to refer to the desired directions of contraction for the contracting layer 214. For example, if the first orientation line 227 is oriented parallel to the opening 120, the desired direction of contraction may be parallel to the second orientation line 229 and perpendicular to the first orientation line 227. Generally, the contracting layer 214 may be placed at the tissue site 102 so that the first orientation line 227 is parallel to the opening 120 and may cover portions of the tissue surface 105 on both sides of the opening 120. In some embodiments, the first orientation line 227 may be coincident with the opening 120. The contracting layer 214 may include a plurality of holes 228 or perforations extending through the contracting layer 214. In sonic embodiments, the walls 230 of the holes 228 may extend through the contracting layer 214 parallel to the thickness 126 of the contracting layer 214. In some embodiments, the holes 228 may have a circular shape as shown.

Figure 8A:
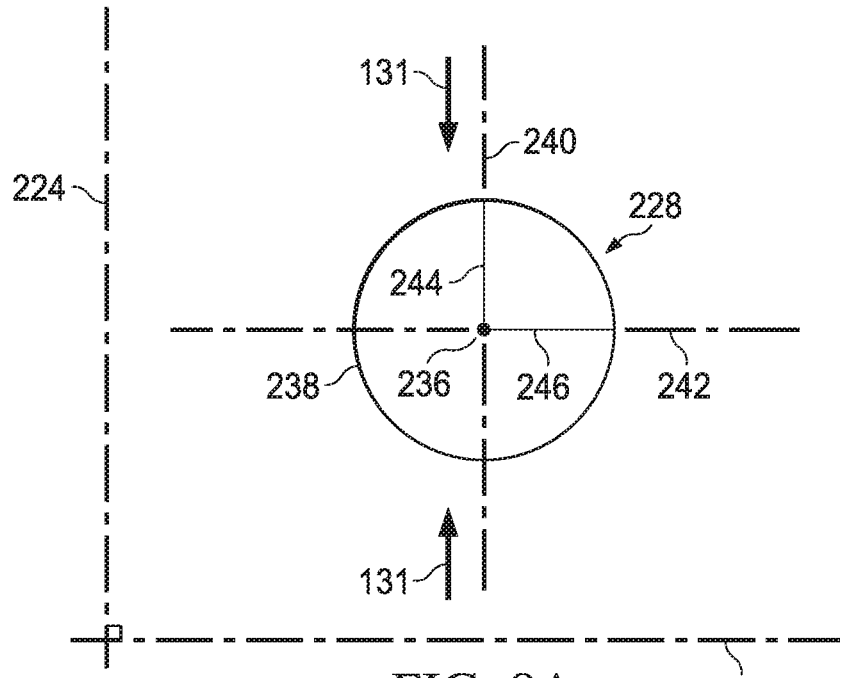
FIG. 8A is a schematic view, illustrating details that may be associated with some embodiments of a hole of the contracting layer of FIG. 7.

Referring more specifically to FIG. 8A, a single hole 228 having a circular shape is shown. The hole 228 may include a center 236, a perimeter 238, and the perforation shape factor (PSF). For reference, the hole 228 may have an X-axis 242 extending through the center 236 parallel to the first orientation line 227, and a Y-axis 240 extending through the center 236 parallel to the second orientation line 229. In some embodiments, the perforation shape factor (PSF) of the hole 228 may be defined as a ratio of a line segment 244 on the Y-axis 240 extending from the center 236 to the perimeter 238 of the hole 228, to a line segment 246 on the X-axis 242 extending from the center 236 to the perimeter 238 of the hole 228. If a length of the line segment 244 is 2.5 mm and the length of the line segment 246 is 2.5 mm, the perforation shape factor (PSF) would be 2.5/2.5 or about 1.

Figure 8B:
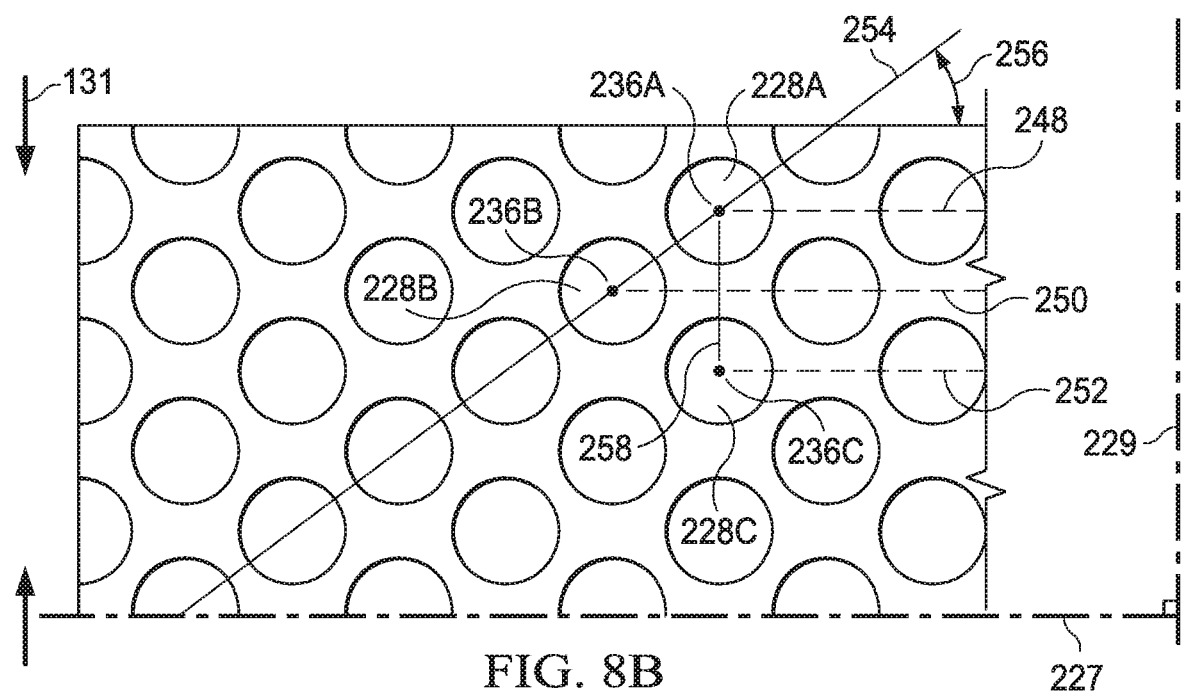
FIG. 8B is a plan view, illustrating details that may be associated with some embodiments of the holes of the contracting layer of FIG. 7.

Referring to FIG. 8B, a portion of the contracting layer 214 of FIG. 7 is shown. The contracting layer 214 may include the plurality of holes 228 aligned in a pattern of parallel rows. The pattern of parallel rows may include a first row 248 of the holes 228, a second row 250 of the holes 228, and a third row 252 of the holes 228. The X-axis 242 of FIG. 8A of each hole 228 may be parallel to the first orientation line 227 of FIG. 8B. The centers 236 of the holes 228 in adjacent rows, for example, the first row 248 and the second row 250, may be characterized by being offset from the second orientation line 229 along the first orientation line 227. In some embodiments, a line connecting the centers of adjacent rows may form the strut angle (SA) with the first orientation line 227. For example, a first hole 228A in the first row 248 may have a center 236A, and a second hole 228B in the second row 250 may have a center 236B. A strut line 254 may connect the center 236A with the center 236B. The strut line 254 may form an angle 256 with the first orientation line 227. The angle 256 may be the strut angle (SA) of the contracting layer 214. In some embodiments, the strut angle (SA) may be less than about 90°. In other embodiments, the strut angle (SA) may be between about 30° and about 70° relative to the first orientation line 227. As described above, if negative pressure is applied to the contracting layer 214, the contracting layer 214 may be more compliant or compressible in a direction perpendicular to the first orientation line 227. By increasing the compressibility of the contracting layer 214 in a direction perpendicular to the first orientation line 227, the contracting layer 214 may collapse to apply a closing three to the opening 120 of the tissue site 102, as described in more detail below.

In some embodiments, the centers 236 of the holes 228 in alternating rows, for example, the center 236A of the first hole 228A in the first row 248 and a center 236C of a hole 228C in the third row 252, may be spaced from each other parallel to the second orientation line 229 by a length 258. In some embodiments, the length 258 may be greater than an effective diameter of the hole 228. If the centers 236 of holes 228 in alternating rows are separated by the length 258, the walls 230 parallel to the first orientation line 227 may be considered continuous. Generally, the walls 230 may be continuous if the walls 230 do not have any discontinuities or breaks between holes 228.

Regardless of the shape of the holes 228, the holes 228 in the contracting layer 214 may leave void spaces in the contracting layer 214 and on the surface of the contracting layer 214 so that only walls 230 of the contracting layer 214 remain with a surface available to contact the tissue surface 105. It may be desirable to minimize the walls 230 so that the holes 228 collapse, causing the contracting layer 214 to collapse to generate the closing force 131 in a direction perpendicular to the first orientation line 227. However, it may also be desirable not to minimize the walls 230 so much that the contracting layer 214 becomes too fragile for sustaining the application of a negative pressure. The void space percentage (VS) of the holes 228 may be equal to the percentage of the volume or surface area of the void spaces created by the holes 228 to the total volume or surface area of the contracting layer 214. In some embodiments, the void space percentage (VS) may be between about 40% and about 60%. In other embodiments, the void space percentage (VS) may be about 54%.

In some embodiments, a diameter of the holes 228 may be selected to permit flow of particulates through the holes 228. In some embodiments, each hole 228 may have a diameter of about 5 mm. In other embodiments, each hole 228 may have an effective diameter between about 3.5 mm and about 20 mm.

Referring now to both FIGS. 7 and 8B, the holes 228 may form a pattern depending on the geometry of the holes 228 and the alignment of the holes 228 between adjacent and alternating rows in the contracting layer 214 with respect to the first orientation line 227. If the contracting layer 214 is subjected to negative pressure, the holes 228 of the contracting layer 214 may collapse. In some embodiments, the void space percentage (VS), the perforation shape factor (PSF), and the strut angle (SA) may cause the contracting layer 214 to collapse along the second orientation line 229 perpendicular to the first orientation line 227. If the contracting layer 214 is positioned on the tissue surface 105 of the tissue site 102 so that the first orientation line 227 coincides with the opening 120, the contracting layer 214 may generate the closing force 131 along the second orientation line 229 such that the tissue surface 105 is contracted in the same direction to facilitate closure of the opening 120. The closing force 131 may be optimized by adjusting the factors described above as set forth in Table 1 below. In some embodiments, the holes 228 may be circular, have a strut angle (SA) of approximately 37°, a void space percentage (VS) of about 54%, a firmness factor (FF) of 5, a perforation shape factor (PSF) of 1, and a diameter of about 5 mm. If the contracting layer 214 is subjected to a negative pressure of about −125 mm Hg, the contracting layer 214 may assert the dosing force 131 of approximately 11.9 N. If the diameter of the holes 228 of the contracting layer 214 is increased to 20 mm, the void space percentage (VS) changed to 52%, the strut angle (SA) changed to 52°, and the perforation shape factor (PSF) and the firmness factor (FF) remain the same, the closing force 131 may be decreased to about 6.5 N.

Figure 9A:
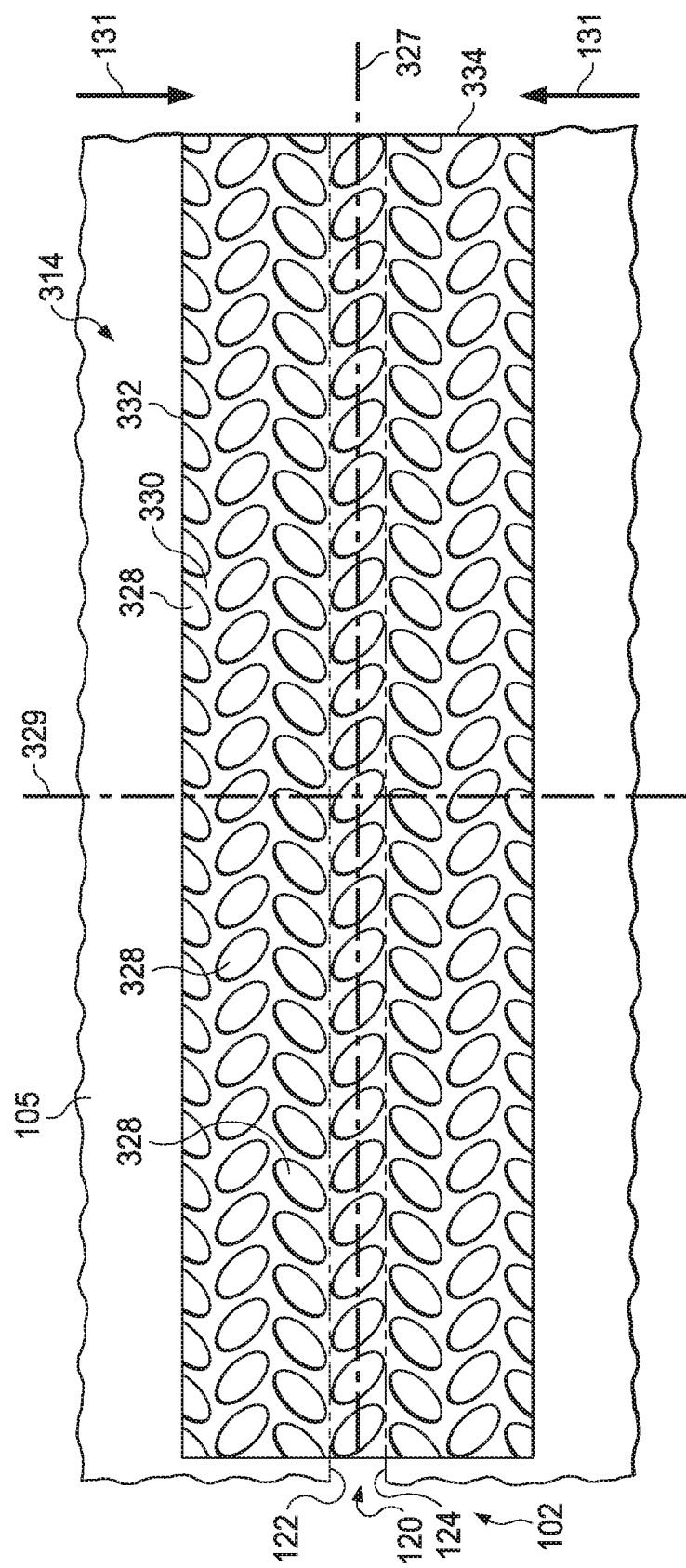
FIG. 9A is a plan view, illustrating details that may be associated with some embodiments of another contracting layer of the negative-pressure therapy system of FIG. 1.

FIG. 9A is a plan view, illustrating additional details that may be associated with some embodiments of a contracting layer 314. The contracting layer 314 may be similar to the contracting layer 114 and operate as described above with respect to FIGS. 1-6. Similar elements may have similar reference numbers indexed to 300. The contracting layer 314 may cover the opening 120 in the tissue surface 105 of the tissue site 102. In some embodiments, the contracting layer 314 may have a first orientation line 327 and a second orientation line 329 that is perpendicular to the first orientation line 327. In some embodiments, the first orientation line 327 and the second orientation line 329 may be used to refer to the desired directions of contraction for the contracting layer 314. For example, if the first orientation line 327 is oriented parallel to the opening 120, the desired direction of contraction may be parallel to the second orientation line 329 and perpendicular to the first orientation line 327. Generally, the contracting layer 314 may be placed at the tissue site 102 so that the first orientation line 327 is parallel to the opening 120 and may cover portions of the tissue surface 105 on both sides of the opening 120. In some embodiments, the first orientation line 327 may be coincident with the opening 120. The contracting layer 314 may include a plurality of holes 328 or perforations extending through the contracting layer 314. In some embodiments, the walls 330 of the holes 328 may extend through the contracting layer 314 parallel to the thickness 126 of the contracting layer 314. In some embodiments, the holes 328 may have an ovoid shape as shown.

Figure 10:
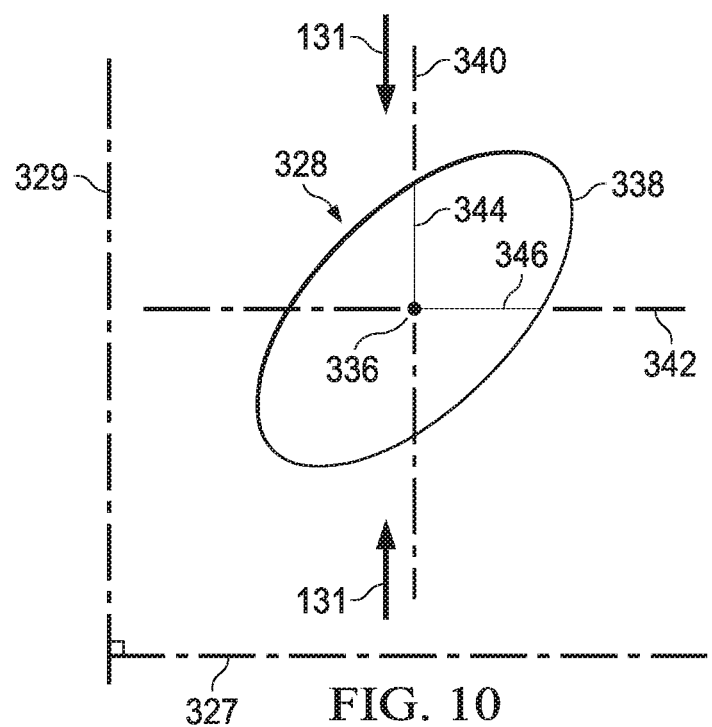
FIG. 10 is a schematic view, illustrating details that may be associated with some embodiments of a hole of the contracting layer of FIG. 9A having a perforation shape factor.

Referring more specifically to FIG. 10, a single hole 328 having an ovoid shape is shown. The hole 328 may include a center 336, a perimeter 338, and a perforation shape factor (PSF). For reference, the hole 328 may have an X-axis 342 extending through the center 336 parallel to the first orientation line 327, and a Y-axis 340 extending through the center 336 parallel to the second orientation line 329. In some embodiments, the perforation shape factor (PSF) of the hole 328 may be defined as a ratio of a line segment 344 on the Y-axis 340 extending from the center 336 to the perimeter 338 of the hole 328, to a line segment 346 on the X-axis 342 extending from the center 336 to the perimeter 338 of the hole 328. If a length of the line segment 344 is 2.5 mm and the length of the line segment 346 is 2.5 mm, the perforation shape factor (PSF) would be 2.5/2.5 or about 1.

Figure 11:
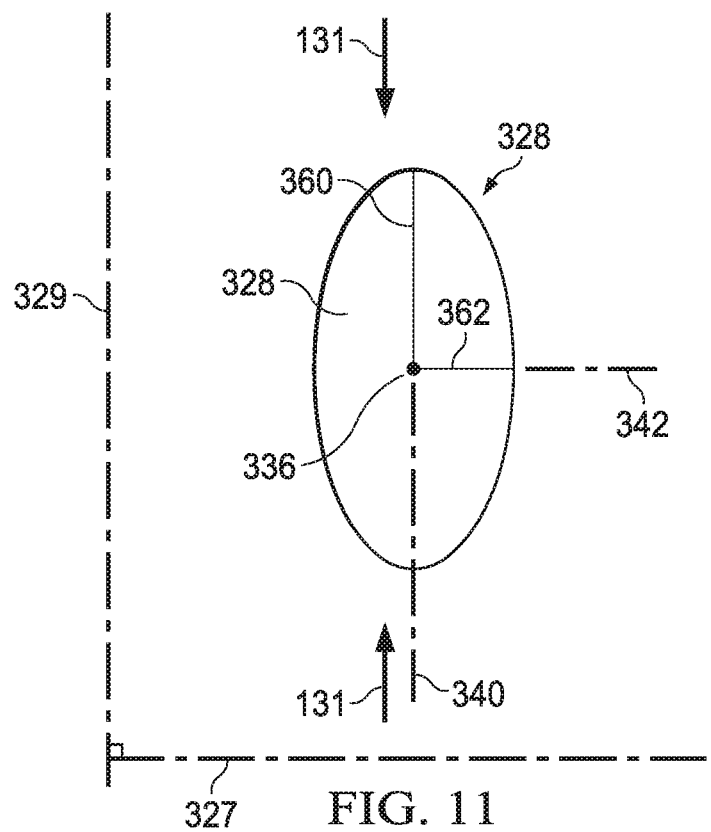
FIG. 11 is a schematic view, illustrating details that may be associated with some embodiments of a hole of the contracting layer of FIG. 9A having another perforation shape factor.

Referring to FIG. 11, if the hole 328 is rotated relative to the first orientation line 327 and the second orientation line 329 so that a major axis of the hole 328 is parallel to the second orientation line 329 and a minor axis of the hole 328 is parallel to the first orientation line 327, the perforation shape factor (PSF) may change. For example, the perforation shape factor (PSF) is now the ratio of a line segment 360 on the Y-axis 340 extending from the center 336 to the perimeter 338 of the hole 328, to a line segment 362 on the X-axis 342 extending from the center 336 to the perimeter 338 of the hole 328. If a length of the line segment 360 is 5 mm and the length of the line segment 362 is 2.5 mm, the perforation shape factor (PSF) would be 5/2.5 or about 2.

Figure 12:
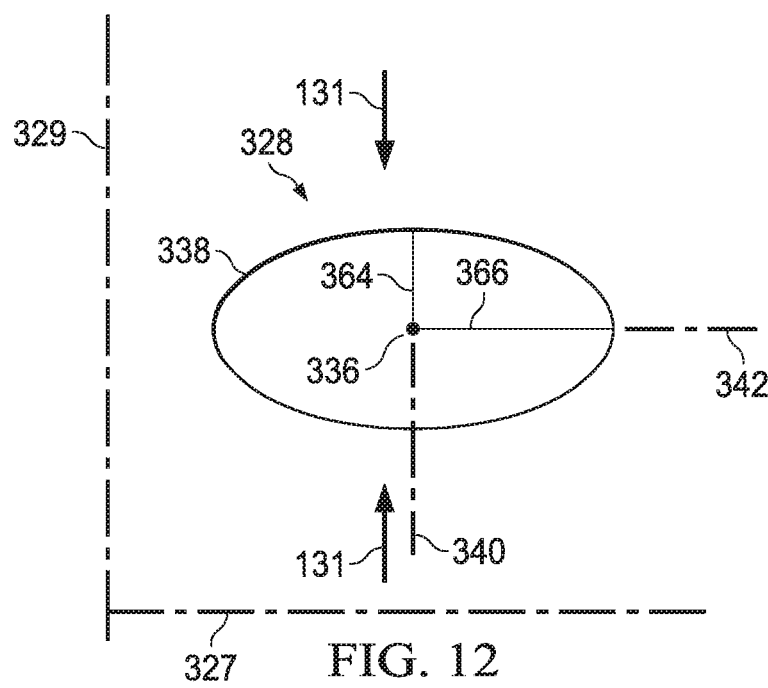
FIG. 12 is a schematic view, illustrating details that may be associated with some embodiments of a hole of the contracting layer of FIG. 9A having another perforation shape factor.

Referring to FIG. 12, if the hole 328 is rotated relative to the first orientation line 327 and the second orientation line 329 so that a major axis of the hole 328 is parallel to the first orientation line 327 and a minor axis of the hole 328 is parallel to the second orientation line 329, the perforation shape factor (PSF) may change. For example, the perforation shape factor (PSF) is now the ratio of a line segment 364 on the Y-axis 340 extending from the center 336 to the perimeter 338 of the hole 328, to a line segment 366 on the X-axis 342 extending from the center 336 to the perimeter 338 of the hole 328. If a length of the line segment 364 is 2.5 mm and the length of the line segment 366 is 5 mm, the perforation shape factor (PSF) would be 2.5/5 or about ½.

Figure 9B:
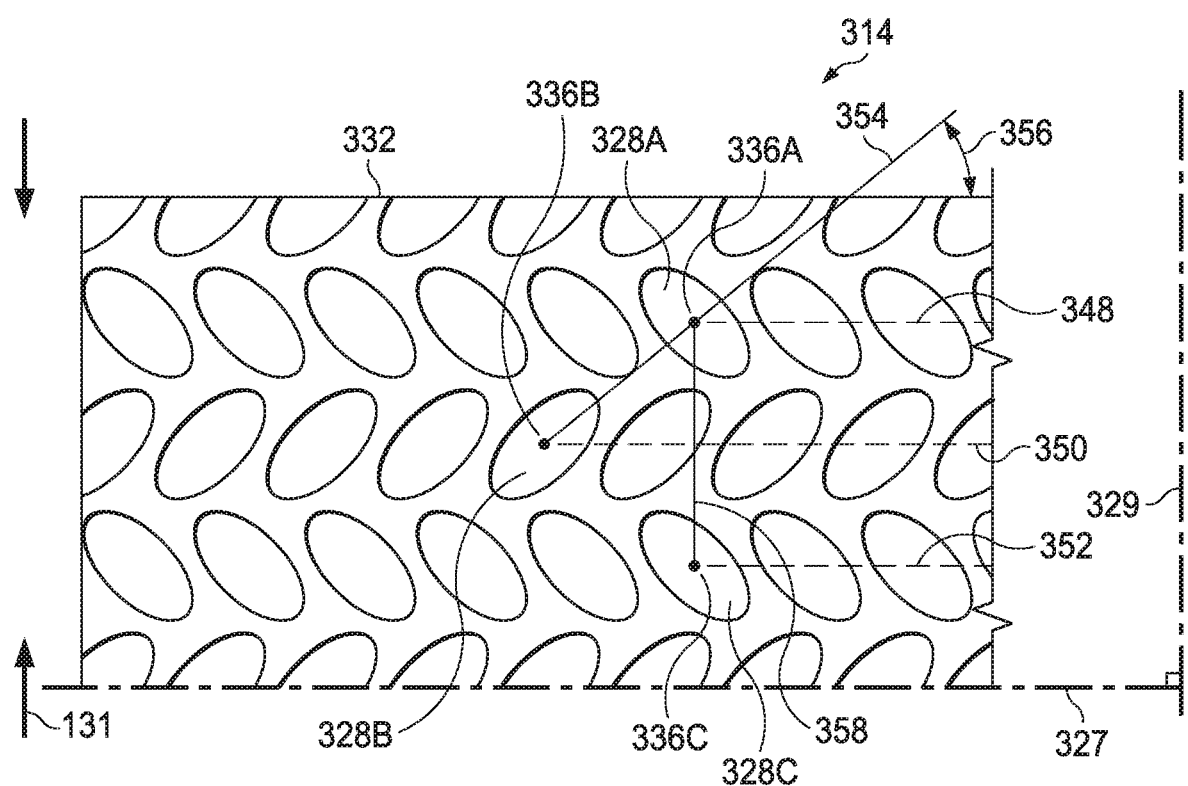
FIG. 9B is a plan view, illustrating details that may be associated with some embodiments of the holes of the contracting layer of FIG. 9A.

Referring to FIG. 9B, a portion of the contracting layer 314 of FIG. 9A is shown. The contracting layer 314 may include the plurality of holes 328 aligned in a pattern of parallel rows. The pattern of parallel rows may include a first row 348 of the holes 328, a second row 350 of the holes 328, and a third row 352 of the holes 328. The X-axis 342 of FIGS. 10, 11, and 12 of each hole 328 may be parallel to the first orientation line 327 of FIG. 9B. The centers 336 of the holes 328 in adjacent rows, for example, the first row 348 and the second row 350, may be characterized by being offset from the second orientation line 329 along the first orientation line 327. In some embodiments, a line connecting the centers of adjacent rows may form a strut angle (SA) with the first orientation line 327. For example, a first hole 328A in the first row 348 may have a center 336A, and a second hole 328B in the second row 350 may have a center 336B. A strut line 354 may connect the center 336A with the center 336B. The strut line 354 may form an angle 356 with the first orientation line 327. The angle 356 may be the strut angle (SA) of the contracting layer 314. In some embodiments, the strut angle (SA) may be less than about 90°. In other embodiments, the strut angle (SA) may be between about 30° and about 70° relative to the first orientation line 327. As described above, if negative pressure is applied to the contracting layer 314, the contracting layer 314 may be more compliant or compressible in a direction perpendicular to the first orientation line 327. By increasing the compressibility of the contracting layer 314 in a direction perpendicular to the first orientation line 327, the contracting layer 314 may collapse to apply the closing force 131 to the opening 120 of the tissue site 102, as described in more detail below.

In some embodiments, the centers 336 of the holes 328 in alternating rows, for example, the center 336A of the first hole 328A in the first row 348 and a center 336C of a hole 328C in the third row 352, may be spaced from each other parallel to the second orientation line 329 by a length 358. In some embodiments, the length 358 may be greater than an effective diameter of the hole 328. If the centers 336 of holes 328 in alternating rows are separated by the length 358, the walls 330 parallel to the first orientation line 327 may be considered continuous. Generally, the walls 330 may be continuous if the walls 330 do not have any discontinuities or breaks between holes 328.

Regardless of the shape of the holes 328, the holes 328 in the contracting layer 314 may leave void spaces in the contracting layer 314 and on the surface of the contracting layer 314 so that only walls 330 of the contracting layer 314 remain with a surface available to contact the tissue surface 105. It may be desirable to minimize the walls 330 so that the holes 328 may collapse, causing the contracting layer 314 to collapse the closing force 131 in a direction perpendicular to the first orientation line 327. However, it may also be desirable not to minimize the walls 330 so much that the contracting layer 314 becomes too fragile for sustaining the application of a negative pressure. The void space percentage (VS) of the holes 328 may be equal to the percentage of the volume or surface area of the void spaces created by the holes 328 to the total volume or surface area of the contracting layer 314. In some embodiments, the void space percentage (VS) may be between about 40% and about 60%. In other embodiments, the void space percentage (VS) may be about 56%.

In some embodiments, an effective diameter of the holes 328 may be selected to permit flow of particulates through the holes 328. In some embodiments, each hole 328 may have an effective diameter of about 7 mm. In other embodiments, each hole 328 may have an effective diameter between about 2.5 mm and about 20 mm.

Referring now to both FIGS. 9A and 9B, the holes 328 may form a pattern depending on the geometry of the holes 328 and the alignment of the holes 328 between adjacent and alternating rows in the contracting layer 314 with respect to the first orientation line 327. If the contracting layer 314 is subjected to negative pressure, the holes 328 of the contracting layer 314 may collapse, causing the contracting layer 314 to collapse along the second orientation line 329 perpendicular to the first orientation line 327. If the contracting layer 314 is positioned on the tissue surface 105 of the tissue site 102 so that the first orientation line 327 coincides with the opening 120, the contracting layer 314 may generate the closing force 131 along the second orientation line 329 such that the tissue surface 105 is contracted in the same direction to facilitate closure of the opening 120. The closing force 131 may be optimized by adjusting the factors described above as set forth in Table 1 below. In some embodiments, the holes 328 may be ovular, have a strut angle (SA) of approximately 47°, a void space percentage (VS) of about 56%, a firmness factor (FF) of 5, a perforation shape factor (PSF) of 1, and an effective diameter of about 7 mm (where the major axis is about 10 mm and the minor axis is about 5 mm). If the contracting layer 314 is subjected to a negative pressure of about −125 mm Hg, the contracting layer 314 may assert the closing force 131 of approximately 13.5 N.

Figure 13A:
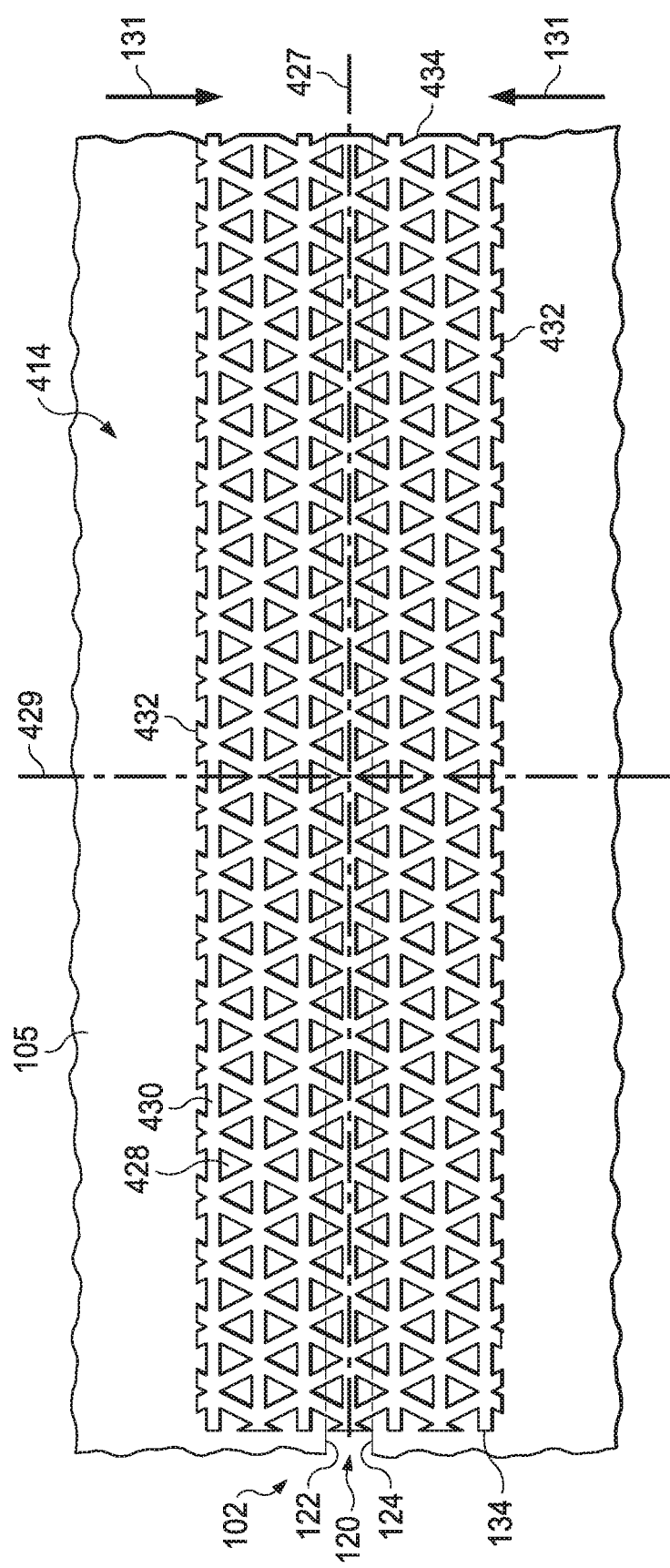
FIG. 13A is a plan view, illustrating details that may be associated with some embodiments of another contracting layer of the negative-pressure therapy system of FIG. 1.

FIG. 13A is a plan view, illustrating additional details that may be associated with some embodiments of a contracting layer 414. The contracting layer 414 may be similar to the contracting layer 114 and operate as described with respect to FIGS. 1-6. Similar elements may have similar reference numbers indexed to 400. For example, the contracting layer 414 is shown as having a generally rectangular shape including longitudinal edges 432 and latitudinal edges 434. The contracting layer 414 may cover the opening 120 in the tissue surface 105 of the tissue site 102. In some embodiments, the contracting layer 414 may have a first orientation line 427 and a second orientation line 429 that is perpendicular to the first orientation line 427. In some embodiments, the first orientation line 427 and the second orientation line 429 may be used to refer to the desired directions of contraction for the contracting layer 414. For example, if the first orientation line 427 is oriented parallel to the opening 120, the desired direction of contraction may be parallel to the second orientation line 429 and perpendicular to the first orientation line 427. Generally, the contracting layer 414 may be placed at the tissue site 102 so that the first orientation line 427 is parallel to the opening 120 and may cover portions of the tissue surface 105 on both sides of the opening 120. In some embodiments, the first orientation line 427 may be coincident with the opening 120. The contracting layer 414 may include a plurality of holes 428 or perforations extending through the contracting layer 414. In some embodiments, the walls 430 of the holes 428 may extend through the contracting layer 414 parallel to the thickness 126 of the contracting layer 414. In some embodiments, the holes 428 may have a triangular shape as shown.

Figure 14:
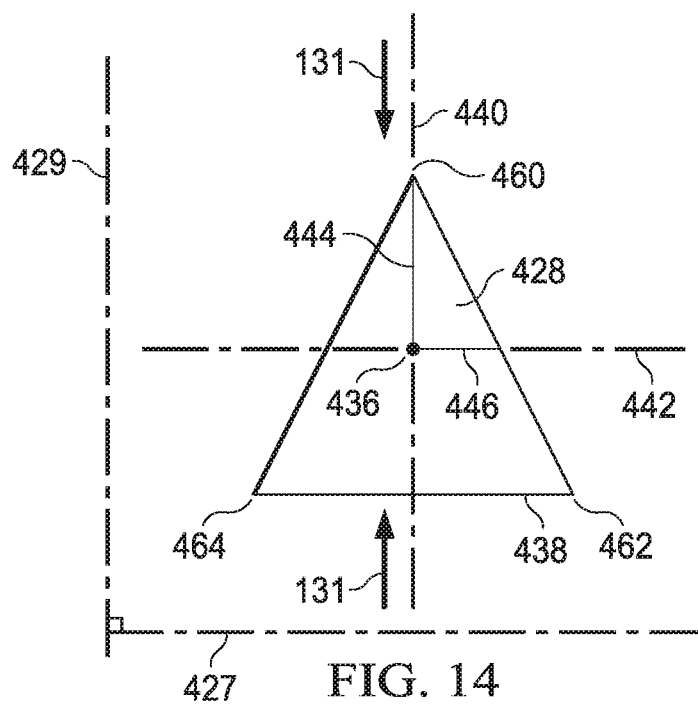
FIG. 14 is a schematic view, illustrating details that may be associated with some embodiments of a hole of the contracting layer of FIG. 13A.

Referring more specifically to FIG. 14, a single hole 428 having a triangular shape is shown. The hole 428 may include a center 436, a perimeter 438, and a perforation shape factor (PSF). In some embodiments, the hole 428 may include a first vertex 460, a second vertex 462, and a third vertex 464. For reference, the hole 428 may have an X-axis 442 extending through the center 436 parallel to the first orientation line 427, and a Y-axis 440 extending through the center 436 parallel to the second orientation line 429. In some embodiments, the perforation shape factor (PSF) of the hole 428 may be defined as a ratio of a line segment 444 on the Y-axis 440 extending from the center 436 to the perimeter 438 of the hole 428, to a line segment 446 on the X-axis 442 extending from the center 436 to the perimeter 438 of the hole 428. If a length of the line segment 444 is 1.1 mm and the length of the line segment 446 is 1 mm, the perforation shape factor (PSF) would be 1.1/1 or about 1.1.

Figure 13B:
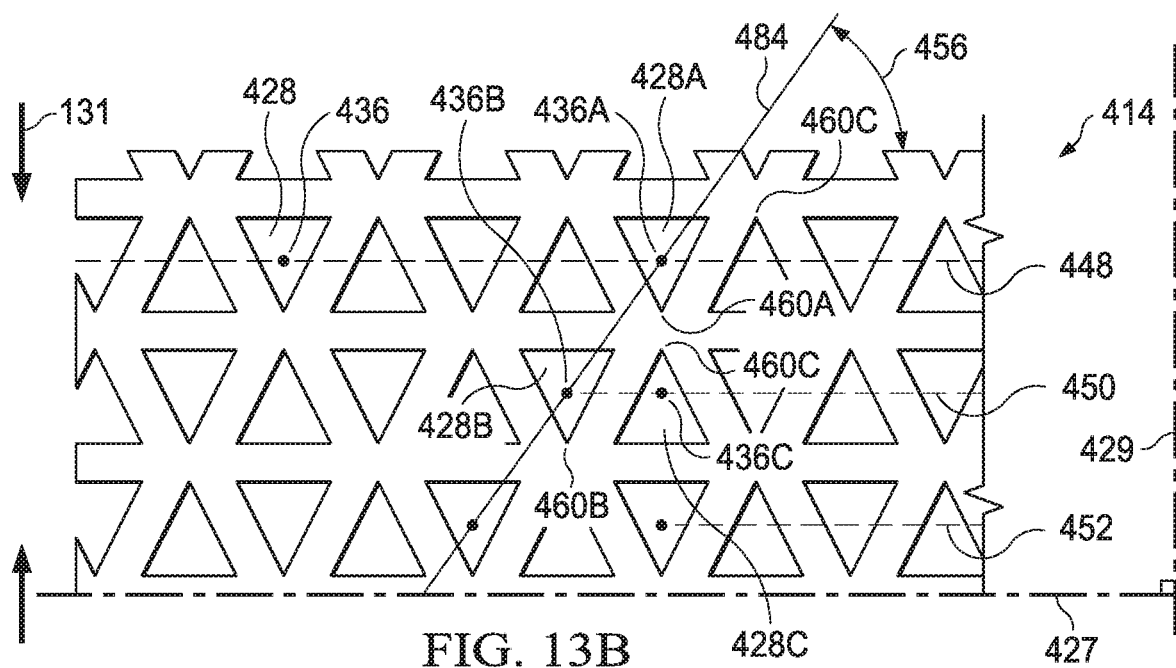
FIG. 13B is a plan view, illustrating details that may be associated with some embodiments of the holes of the contracting layer of FIG. 13A.

Referring to FIG. 13B, a portion of the contracting layer 414 of FIG. 13A is shown. The contracting layer 414 may include the plurality of holes 428 aligned in a pattern of parallel rows. The pattern of parallel rows may include a first row 448 of the holes 428, a second row 450 of the holes 428, and a third row 452 of the holes 428. The X-axis 442 of FIG. 14 of each hole 428 may be parallel to the first orientation line 427 of FIG. 13B. In some embodiments, a first hole 428A in the first row 448 may be oriented so that the first vertex 460A of a first hole 428A may be between the first orientation line 427 and a leg of the first hole 428A opposite the first vertex 460A. A hole 428C that is adjacent the first hole 428A in the first row 448 may be oriented so that the first vertex 460C may be oriented opposite the first hole 428A.

The centers 436 of the holes 428 in adjacent rows having the first vertex 460 oriented in a same direction, for example, the first row 448 and the second row 450, may be characterized by being offset from the second orientation line 429 along the first orientation line 427. In some embodiments, a line connecting the centers of adjacent rows may form a strut angle (SA) with the first orientation line 427. For example, a first hole 428A in the first row 448 may have a center 436A, and a second hole 428B in the second row 450 may have a center 436B and a first vertex 460B. A strut line 454 may connect the center 436A with the center 436B. The strut line 454 may form an angle 456 with the first orientation line 427. The angle 456 may be the strut angle (SA) of the contracting layer 414. In some embodiments, the strut angle (SA) may be less than about 90°. In other embodiments, the strut angle (SA) may be between about 40° and about 70° relative to the first orientation line 427. As described above, if negative pressure is applied to the contracting layer 414, the contracting layer 414 may be more compliant or compressible in a direction perpendicular to the first orientation line 427. By increasing the compressibility of the contracting layer 414 in a direction perpendicular to the first orientation line 427, the contracting layer 414 may collapse to apply the closing force 131 to the opening 120 of the tissue site 102, as described in more detail below.

Regardless of the shape of the holes 428, the holes 428 in the contracting layer 414 may leave void spaces in the contracting layer 414 and on the surface of the contracting layer 414 so that only walls 430 of the contracting layer 414 remain with a surface available to contact the tissue surface 105. It may be desirable to minimize the walls 430 so that the holes 428 may collapse, causing the contracting layer 414 to generate the closing force 131 in a direction perpendicular to the first orientation line 427. However, it may also be desirable not to minimize the walls 430 so much that the contracting layer 414 becomes too fragile for sustaining the application of a negative pressure. The void space percentage (VS) of the holes 428 may be equal to the percentage of the volume or surface area of the void spaces created by the holes 428 to the total volume or surface area of the contracting layer 414. In some embodiments, the void space percentage (VS) may be between about 40% and about 60%. In other embodiments, the void space percentage (VS) may be about 56%.

In some embodiments, an effective diameter of the holes 428 may be selected to permit flow of particulates through the holes 428. In some embodiments, each hole 428 may have an effective diameter of about 7 mm. In other embodiments, each hole 428 may have an effective diameter between about 2.5 mm and about 20 mm.

Referring now to both FIGS. 13A and 13B, the holes 428 may form a pattern depending on the geometry of the holes 428 and the alignment of the holes 428 between adjacent and alternating rows in the contracting layer 414 with respect to the first orientation line 427. If the contracting layer 414 is subjected to negative pressure, the holes 428 of the contracting layer 414 may collapse. In some embodiments, the void space percentage (VS), the perforation shape factor (PSF), and the strut angle (SA) may cause the contracting layer 414 to collapse along the second orientation line 429 perpendicular to the first orientation line 427. If the contracting layer 414 is positioned on the tissue surface 105 of the tissue site 102 so that the first orientation line 427 coincides with the opening 120, the contracting layer 414 may generate the closing force 131 along the second orientation line 429 such that the tissue surface 105 is contracted in the same direction to facilitate closure of the opening 120. The closing force 131 may be optimized by adjusting the factors described above as set forth in Table 1 below. In some embodiments, the holes 428 may be triangular, have a strut angle (SA) of approximately 63°, a void space percentage (VS) of about 40%, a firmness factor (FF) of 5, a perforation shape factor (PSF) of 1.1, and an effective diameter of about 10 mm. If the contracting layer 414 is subjected to a negative pressure of about −125 mm Hg, the contracting layer 414 may assert the closing force 131 of approximately 12.2 N.

Figure 15:
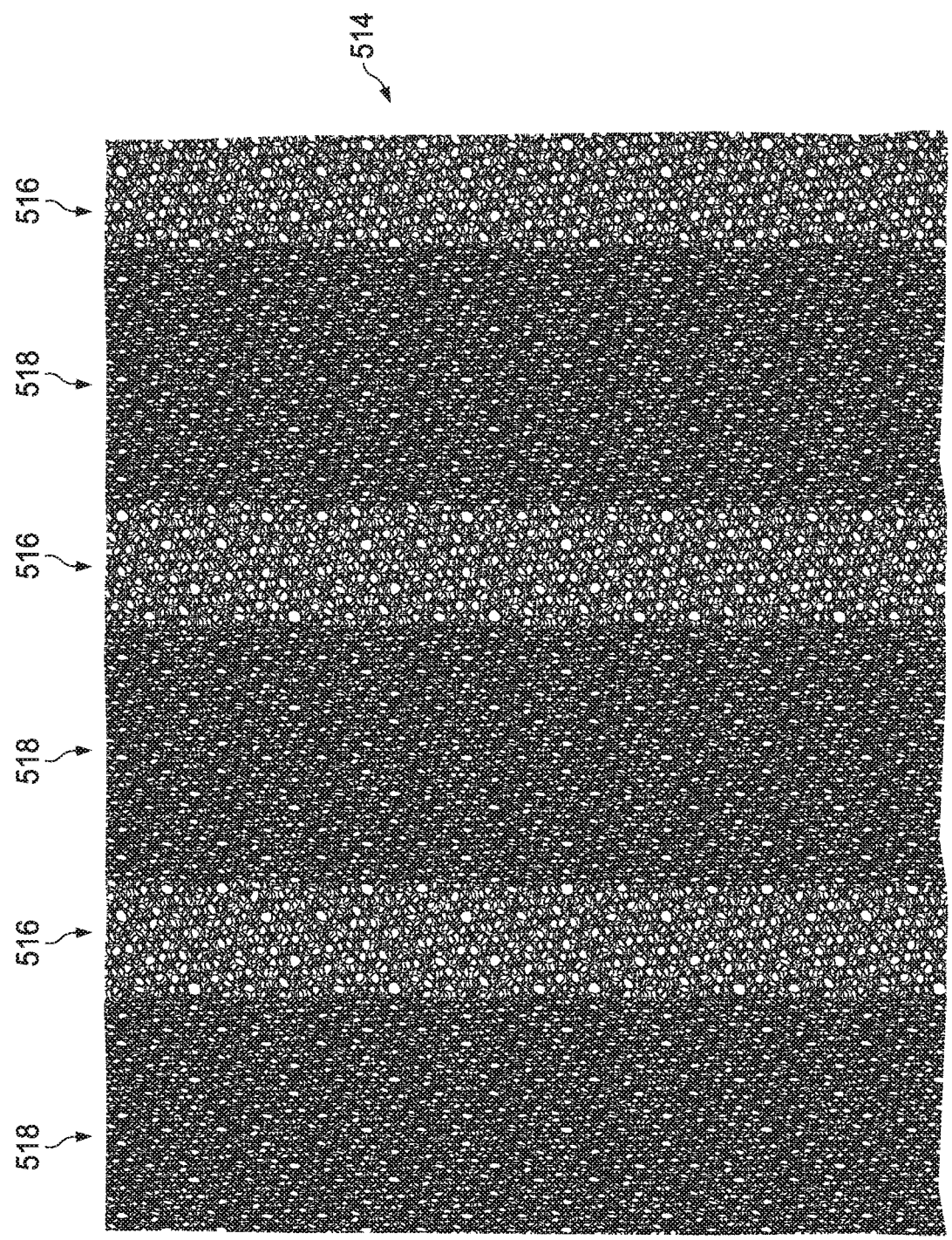
FIG. 15 is a plan view, illustrating details that may be associated with some embodiments of another contracting layer of the negative-pressure therapy system of FIG. 1.

FIG. 15 is a plan view, illustrating additional details that may be associated with sonic embodiments of a contracting layer 514. The contracting layer 514 may be similar to the contracting layer 114 described above with respect to FIGS. 1-6. The contracting layer 514 may include stripes 516 having a first density and stripes 518 having a second density. In sonic embodiments, the stripes 516 and the stripes 518 may be vertically oriented relative to a tissue site, and in other embodiments, the stripes 516 and the stripes 518 may be horizontally oriented relative to a tissue site. In still other embodiments, the stripes 516 and the stripes 518 may be oriented at an angle relative to a tissue site. In some embodiments, the second density may be greater than the first density. In some embodiments, the second density may be between about 3 times and about 5 times greater than the first density. In some embodiments, the contracting layer 514 may be formed from a foam, similar to GranuFoam®. In some embodiments, the stripes 518 may be formed by compressing portions of the foam. For example, the stripes 516 may be an uncompressed foam, and the stripes 518 may be a compressed foam having a firmness factor of about 5. Generally, the stripes 516 may be more compressible than the stripes 518. If the contracting layer 514 is placed under a negative-pressure, the stripes 516 may collapse before the stripes 518. In some embodiments, if the stripes 516 collapse, the contracting layer 514 may compress perpendicular to the stripes 516.

A closing force, such as the closing force 131, generated by a contracting layer, such as the contracting layer 114, may be related to a compressive force generated by applying negative pressure at a therapy pressure to a sealed therapeutic environment. For example, the closing force 131 may be proportional to a product of a therapy pressure (TP) in the sealed therapeutic environment 118, the compressibility factor (CF) of the contracting layer 114, and a surface area (A) of the contracting layer 114. The relationship is expressed as follows:

Closing force α(TP*CF*A)

In some embodiments, the therapy pressure TP is measured in N/m², the compressibility factor (CF) is dimensionless, the area (A) is measured in m², and the closing force is measured in Newtons (N). The compressibility factor (CF) resulting from the application of negative pressure to a contracting layer may be, for example, a dimensionless number that is proportional to the product of the void space percentage (VS) of a contracting layer, the firmness factor (FF) of the contracting layer, the strut angle (SA) of the holes in the contracting layer, and the perforation shape factor (PSF) of the holes in the contracting layer. The relationship is expressed as follows:

Compressibility Factor(CF)α(VS*FF*sin(SA)*PSF)

Based on the above formulas, contracting layers formed from different materials with holes of different shapes were manufactured and tested to determine the closing force of the contracting layers. For each contracting layer, the therapy pressure TP was about 425 mmHg and the dimensions of the contracting layer were about 200 mm by about 53 mm so that the surface area (A) of the contracting layer was about 106 cm² or 0.0106 m². Based on the two equations described above, the closing force for a Supracor® contracting layer 114 having a firmness factor (FF) of 3 was about 13.3 where the Supracor® contracting layer 114 had hexagonal holes 128 with a distance between opposite vertices of 5 mm, a perforation shape factor (PSF) of 1.07, a strut angle (SA) of approximately 66°, and a void space percentage (VS) of about 55%. A similarly dimensioned GranuFoam® contracting layer 114 generated the closing force 131 of about 9.1 Newtons (N).

of the cover 112, the modulus of the tissue site 102, slippage of the cover 112 over the tissue site 102, and friction between the protective layer 116, the contracting layer 114, and the tissue surface 105 of tissue site 102 may cause the actual value of the closing force 131 to be less than the calculated value of the closing force 131.

In some embodiments, the material, the void space percentage (VS), the firmness factor, the strut angle, the hole shape, the perforation shape factor (PSF), and the hole diameter may be selected to increase compression or collapse of the contracting layer 114 in a lateral direction, as shown by the closing force 131, by forming weaker walls 130. Conversely, the factors may be selected to decrease compression or collapse of the contracting layer 114 in a lateral direction, as shown by the closing force 131, by forming stronger walls 130. Similarly, the factors described herein can be selected to decrease or increase the compression or collapse of the contracting layer 114 perpendicular to the closing force 131.

The systems, apparatuses, and methods described herein may provide significant advantages. For example, closing forces generated by the described contracting layers meet or exceed other contracting layers designed for a similar purpose. The described contracting layers may also assist in closure of an incisional tissue site by distributed force along a length of the incisional opening, reducing potential trauma that may be caused by point loading such as with sutures, staples or hooks.

While shown in a few illustrative embodiments, a person having ordinary skill in the art will recognized that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically

TABLE 1

| Material | VS | FF | SA | Hole Shape | PSF | Major diam. (mm) | Closing force |
|---|---|---|---|---|---|---|---|
| GranuFoam® | 56 | 5 | 47 | Ovular | 1 | 10 | 13.5 |
| Supracor® | 55 | 3 | 66 | Hexagon | 1.1 | 5 | 13.3 |
| GranuFoam® | 40 | 5 | 63 | Triangle | 1.1 | 10 | 12.2 |
| GranuFoam® | 54 | 5 | 37 | Circular | 1 | 5 | 11.9 |
| GranuFoam® | 52 | 5 | 37 | Circular | 1 | 20 | 10.3 |
| Grey Foam | N/A | 5 | N/A | Horizontal stripes | N/A | N/A | 9.2 |
| GranuFoam® | 55 | 5 | 66 | Hexagon | 1.1 | 5 | 9.1 |
| GranuFoam® | N/A | 5 | N/A | Horizontal stripes | N/A | N/A | 8.8 |
| Zotefoam | 52 | 3 | 37 | Circular | 1 | 10 | 8.4 |
| GranuFoam® | 52 | 5 | 37 | Circular | 1 | 10 | 8.0 |
| GranuFoam® | 52 | 5 | 64 | Circular | 1 | 10 | 7.7 |
| GranuFoam® | 56 | 5 | 66 | Hexagon | 1.1 | 10 | 7.5 |
| Grey Foam | N/A | 3 | N/A | Horizontal stripes | N/A | N/A | 7.2 |
| Zotefoam | 52 | 3 | 52 | Circular | 1 | 20 | 6.8 |
| GranuFoam® | N/A | 3 | N/A | Horizontal Striping | N/A | N/A | 6.6 |
| GranuFoam® | 52 | 5 | 52 | Circular | 1 | 20 | 6.5 |
| GranuFoam® | N/A | 5 | N/A | Vertical Stripes | N/A | N/A | 6.1 |
| GranuFoam® | N/A | 1 | N/A | None | N/A | N/A | 5.9 |
| GranuFoam® | N/A | 3 | N/A | Vertical stripes | N/A | N/A | 5.6 |
| GranuFoam® | 52 | 1 | 37 | None | 1 | 10 | 5.5 |

In some embodiments, the formulas described above may not precisely describe the closing forces due to losses in force due to the transfer of the force from the contracting layer to the wound. For example, the modulus and stretching recited in detail. For example, certain features, elements, or aspects may be omitted from the claims if not necessary to distinguish the novel and inventive features from what is already known to a person having ordinary skill in the art.

Features, elements, and aspects described herein may also be combined or replaced by alternative features serving the same, equivalent, or similar purpose without departing from the scope of the invention defined by the appended claims.

What is claimed is:

1. A system for closing an opening through a surface of a tissue site, the system comprising:
    a sealing member configured to cover the opening to form a sealed space;
    a negative-pressure source configured to be fluidly coupled to the sealed space to provide negative pressure to the sealed space;
    a protective layer configured to be positioned over the opening; and
    a contracting layer configured to be positioned over the opening and between the protective layer and the sealing member, the contracting layer formed from a material having a plurality of holes extending through the contracting layer to form a void space, the holes having a perforation shape factor and a strut angle configured to cause the plurality of holes to collapse in a direction substantially perpendicular to the opening,
    wherein the contracting layer is configured to generate a closing force substantially parallel to the surface of the tissue site to close the opening in response to application of the negative pressure.

2. The system of claim 1, wherein the plurality of holes are formed in two or more parallel rows.

3. The system of claim 1, wherein the strut angle is an angle between a line connecting centers of holes in adjacent rows and an orientation line perpendicular to a direction of the closing force, and the strut angle is about 90 degrees.

4. The system of claim 1, wherein the strut angle is an angle between a line connecting centers of holes in adjacent rows and an orientation line perpendicular to a direction of the closing force, and the strut angle is less than about 90 degrees.

5. The system of claim 1, wherein the perforation shape factor of a hole of the plurality of holes is a ratio of a first line segment to a second line segment, the first line segment extending from a center of the hole to a perimeter of the hole in a direction perpendicular to a direction of the closing force and the second line segment extending from a center of the hole to a perimeter of the hole in a direction parallel to the direction of the closing force, and wherein the perforation shape factor of the hole is less than about 1.

6. The system of claim 1, wherein the perforation shape factor of a hole of the plurality of holes is a ratio of a first line segment to a second line segment, the first line segment extending from a center of the hole to a perimeter of the hole in a direction perpendicular to a direction of the closing force and the second line segment extending from a center of the hole to a perimeter of the hole in a direction parallel to the direction of the closing force, and wherein the perforation shape factor of the hole is more than about 1.

7. The system of claim 1, wherein the material is a foam material having a firmness factor, the firmness factor is a ratio of density of the foam material in a compressed state to a density of the foam material in an uncompressed state, and the firmness factor is about 5.

8. The system of claim 1, wherein the material is a foam material having a firmness factor, the firmness factor is a ratio of density of the foam material in a compressed state to a density of the foam material in an uncompressed state, and the firmness factor is about 3.

9. The system of claim 1, wherein the protective layer is configured to be positioned between the contracting layer and at least a portion of the surface of the tissue site surrounding the opening.

10. An apparatus for closing an opening through a surface of a tissue site, the apparatus comprising:
    a contracting layer configured to be positioned over the opening and formed from a material having a plurality of holes extending through the contracting layer to form a void space, the holes having a perforation shape factor and a strut angle configured to cause the plurality of holes to collapse in a direction substantially perpendicular to the opening,
    wherein the contracting layer is configured to generate a closing force substantially parallel to the surface of the tissue site to close the opening in response to application of a negative pressure.

11. The apparatus of claim 10, wherein the plurality of holes are formed in two or more parallel rows.

12. The apparatus of claim 10, wherein the strut angle is an angle between a line connecting centers of holes in adjacent rows and an orientation line perpendicular to a direction of the closing force, and the strut angle is about 90 degrees.

13. The apparatus of claim 10, wherein the strut angle is an angle between a line connecting centers of holes in adjacent rows and an orientation line perpendicular to a direction of the closing force, and the strut angle is less than about 90 degrees.

14. The apparatus of claim 10, wherein the perforation shape factor of a hole of the plurality of holes is a ratio of a first line segment to a second line segment, the first line segment extending from a center of the hole to a perimeter of the hole in a direction perpendicular to a direction of the closing force and the second line segment extending from a center of the hole to a perimeter of the hole in a direction parallel to the direction of the closing force, and wherein the perforation shape factor of the hole is less than about 1.

15. The apparatus of claim 10, wherein the perforation shape factor of a hole of the plurality of holes is a ratio of a first line segment to a second line segment, the first line segment extending from a center of the hole to a perimeter of the hole in a direction perpendicular to a direction of the closing force and the second line segment extending from a center of the hole to a perimeter of the hole in a direction parallel to the direction of the closing force, and wherein the perforation shape factor of the hole is more than about 1.

16. The apparatus of claim 10, wherein the material is a foam material having a firmness factor, wherein the firmness factor is a ratio of density of the foam material in a compressed state to a density of the foam material in an uncompressed state, and the firmness factor is about 5.

17. The apparatus of claim 10, wherein the material is a foam material having a firmness factor, wherein the firmness factor is a ratio of density of the foam material in a compressed state to a density of the foam material in an uncompressed state, and the firmness factor is about 3.

18. A method for closing an opening through a surface of a tissue site, the method comprising:
    positioning a contracting layer over the opening, the contracting layer formed from a material having a plurality of holes extending through the contracting layer to form a void space, the plurality of holes having a perforation shape factor and a strut angle;
    applying negative pressure to the contracting layer to cause the plurality of holes to collapse in a direction substantially perpendicular to the opening in response to at least one of the perforation shape factor and the strut angle; and collapsing the contracting layer substantially parallel to the surface of the tissue site to close the opening.

19. The method of claim 18, further comprising:

positioning a protective layer over the opening; and positioning a sealing member over the contracting layer to form a sealed space.

20. The method of claim 19, wherein the contracting layer is adjacent the protective layer.

21. The method of claim 18, wherein collapsing the contracting layer comprises drawing edges of the contracting layer toward a center of the contracting layer in response to the collapse of the holes of the contracting layer.

* * * * *

UNITED STATES PATENT AND TRADEMARK OFFICE
CERTIFICATE OF CORRECTION

PATENT NO.         : 10,736,788 B2                                Page 1 of 2
APPLICATION NO.    : 15/958773
DATED              : August 11, 2020
INVENTOR(S)        : Christopher Brian Locke It is certified that error appears in the above-identified patent and that said Letters Patent is hereby corrected as shown below:

On the Title Page

On Page 3, Column 1, Under (Other Publications)
Line 7, delete "Philidelphia," and insert -- Philadelphia, --, therefor.

On Page 4, Column 1, Under (Other Publications)
Line 7, delete "Hypermia" and insert -- Hyperemia --, therefor.

In the Specification

Column 6
Lines 64-65, delete "capralactones." and insert -- caprolactones. --, therefor.

Column 8
Line 5, after "by" insert -- the --.

Column 10
Line 15, delete "sonic" and insert -- some --, therefor.

Column 14
Line 15, delete "sonic" and insert -- some --, therefor.
Line 64, delete "three" and insert -- force --, therefor.

Column 15
Line 61, delete "dosing" and insert -- closing --, therefor.

Column 17
Line 56, delete "dosing" and insert -- closing --, therefor.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*

Column 20
Line 40, delete "sonic" and insert -- some --, therefor.
Line 45, delete "sonic" and insert -- some --, therefor.

Column 21
Line 28, delete "425" and insert -- -125 --, therefor.